(12) United States Patent
Mirkin et al.

(10) Patent No.: US 7,323,309 B2
(45) Date of Patent: Jan. 29, 2008

(54) BIO-BARCODES BASED ON OLIGONUCLEOTIDE-MODIFIED PARTICLES

(75) Inventors: Chad A. Mirkin, Wilmette, IL (US); So-Jung Park, Austin, TX (US); Jwa-Min Nam, Berkeley, CA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/217,106

(22) Filed: Aug. 31, 2005

(65) Prior Publication Data

US 2006/0051798 A1    Mar. 9, 2006

Related U.S. Application Data

(63) Continuation-in-part of application No. 09/820,279, filed on Mar. 28, 2001, now Pat. No. 6,750,016.

(60) Provisional application No. 60/350,560, filed on Nov. 13, 2001, provisional application No. 60/192,699, filed on Mar. 28, 2000.

(51) Int. Cl.
*C12Q 1/68* (2006.01)
*C07H 21/02* (2006.01)
*C07H 21/04* (2006.01)

(52) U.S. Cl. .......... 435/6; 536/23.1; 536/24.3
(58) Field of Classification Search .......... 435/6; 536/23.1, 24.3
See application file for complete search history.

(56) References Cited

U.S. PATENT DOCUMENTS

| | | | |
|---|---|---|---|
| 4,193,983 A | 3/1980 | Ullman et al. | |
| 4,256,834 A | 3/1981 | Zuk et al. | |
| 4,261,968 A | 4/1981 | Ullman et al. | |
| 4,313,734 A | 2/1982 | Leuvering | |
| 4,318,707 A | 3/1982 | Litman et al. | |
| 4,650,770 A | 3/1987 | Liu et al. | |
| 4,713,348 A | 12/1987 | Ullman | |
| 4,853,335 A | 8/1989 | Olsen et al. | |
| 4,868,104 A | 9/1989 | Kura et al. | |
| 4,996,143 A | 2/1991 | Heller et al. ............. 435/6 |
| 5,225,064 A | 7/1993 | Henkens et al. | |
| 5,284,748 A | 2/1994 | Mroczkowski et al. | |

(Continued)

FOREIGN PATENT DOCUMENTS

EP    0 630 974 A2    6/1994

(Continued)

OTHER PUBLICATIONS

Stimpson, et al., "Real-time detection of DNA hybridization and melting on oligonucleotide arrays by using optical wave guides," *Proc. Natl. Acad. Sci..*, vol. 92, pp. 6379-6383, California Instiute of Technology (1995) U.S.

(Continued)

*Primary Examiner*—Jezia Riley
(74) *Attorney, Agent, or Firm*—Gregory T. Pletta

(57) ABSTRACT

The present invention relates to a screening methods, compositions, and kits for detecting for the presence or absence of one or more target analytes, e.g. proteins such as antibodies, in a sample. In particular, the present invention relates to a method that utilizes reporter oligonucleotides as biochemical barcodes for detecting multiple protein structures or other target analytes in one solution.

9 Claims, 4 Drawing Sheets

U.S. PATENT DOCUMENTS

| | | | |
|---|---|---|---|
| 5,288,609 A | 2/1994 | Engelhardt et al. | |
| 5,294,369 A | 3/1994 | Shigekawa et al. | |
| 5,360,895 A | 11/1994 | Hainfield et al. | |
| 5,384,073 A | 1/1995 | Shigekawa et al. | |
| 5,384,265 A | 1/1995 | Kidwell et al. | |
| 5,460,831 A | 10/1995 | Kossovsky et al. | |
| 5,472,881 A | 12/1995 | Beebe et al. | |
| 5,508,164 A | 4/1996 | Kausch et al. | 435/6 |
| 5,514,602 A | 5/1996 | Brooks, Jr. et al. | |
| 5,521,289 A | 5/1996 | Hainfeld et al. | |
| 5,543,158 A | 8/1996 | Gref et al. | |
| 5,571,726 A | 11/1996 | Brooks, Jr. et al. | |
| 5,599,668 A | 2/1997 | Stimpson et al. | |
| 5,609,907 A | 3/1997 | Natan | |
| 5,637,508 A | 6/1997 | Kidwell et al. | |
| 5,665,582 A | 9/1997 | Kaushch et al. | |
| 5,681,943 A | 10/1997 | Letsinger et al. | |
| 5,751,018 A | 5/1998 | Alivisatos et al. | |
| 5,830,986 A | 11/1998 | Merrill et al. | 528/332 |
| 5,900,481 A | 5/1999 | Lough et al. | 536/55.3 |
| 5,922,537 A | 7/1999 | Ewart et al. | 435/6 |
| 5,939,021 A | 8/1999 | Hansen et al. | |
| 5,972,615 A | 10/1999 | An et al. | 435/6 |
| 5,990,479 A | 11/1999 | Weiss et al. | |
| 6,025,202 A | 2/2000 | Natan | |
| 6,149,868 A | 11/2000 | Natan et al. | |
| 6,203,989 B1 | 3/2001 | Goldberg et al. | 435/6 |
| 6,214,560 B1 | 4/2001 | Yguerabide et al. | 435/7.1 |
| 6,251,303 B1 | 6/2001 | Bawendi et al. | 252/301.4 R |
| 6,264,825 B1 | 7/2001 | Blackburn et al. | 205/777.5 |
| 6,277,489 B1 | 8/2001 | Abbott et al. | 428/403 |
| 6,306,610 B1 | 10/2001 | Bawendi et al. | 435/7.1 |
| 6,361,944 B1 | 3/2002 | Mirkin et al. | 435/6 |
| 6,365,418 B1 | 4/2002 | Wagner et al. | 436/518 |
| 6,417,340 B1 | 7/2002 | Mirkin et al. | 536/23.1 |

FOREIGN PATENT DOCUMENTS

| | | |
|---|---|---|
| EP | 0 667 398 A2 | 8/1995 |
| WO | WO 89/06801 | 7/1989 |
| WO | WO 90/02205 | 3/1990 |
| WO | WO 92/04469 | 3/1992 |
| WO | WO 93/10564 | 5/1993 |
| WO | WO 93/25709 | 12/1993 |
| WO | WO 94/29484 | 12/1994 |
| WO | WO 97/40181 | 10/1997 |
| WO | WO 98/04740 | 2/1998 |
| WO | WO 98/10289 | 3/1998 |
| WO | WO 98/17317 | 4/1998 |
| WO | WO 99/23258 | 10/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 00/25136 | 5/2000 |
| WO | WO 01/00876 | 1/2001 |
| WO | WO 01/51665 | 7/2001 |
| WO | WO 01/72123 | 10/2001 |
| WO | WO 01/86301 | 11/2001 |
| WO | WO 02/04681 | 1/2002 |
| WO | WO 02/18643 | 3/2002 |
| WO | WO 02/36169 | 5/2002 |
| WO | WO 00/33079 | 6/2002 |
| WO | WO 02/46472 | 6/2002 |
| WO | WO 02/46483 | 6/2002 |

OTHER PUBLICATIONS

Storhoff, et al., "Strategies for Organizing Nanoparticles into Aggregate Structures and Functional Materials," *Journal of Cluster Science*, vol. 8, No. 3, pp. 179-217, Plenum Publishing Corporation (1997) U.S.

Storhoff, et al., "One-Pot Colorimetric Differentiation of Polynucleotides with Single Base Imperfections Using Gold Nanoparticle Probes," *J. Am Chem. Soc.*, vol. 20, pp. 1961-1964, American Chemical Society (1998) U.S.

Velev, et al., "In Situ Assembly of Colloidal Particles into Miniaturized Biosensors," *Langmuir*, vol. 15, No. 11, pp. 3693-3698, American Chemical Society (1999) U.S.

Zhu, et al., "The First Raman Spectrum of an Organic Monolayer on a High-Temperature Superconductor: Direct Spectroscopic Evidence for a Chemical Interaction between an Amine and $Yba_2Cu_3O_{7-8}$," *J. Am. chem. Soc.*, vol. 119, pp. 235-236, American Chemical Society (1997) U.S.

Yguerabide, et al., "Light-Scattering Submicroscopic Particles as Highly Fluorescent Analogs and Their Use as Tracer Labels in Clinical and Biological Applications," I. Theory, *Analytical Biochemistry*, vol. 262, pp. 137-156 (1998) U.S.

Yguerabide, et al., "Light-Scattering Submicroscopic Particles as Highly Fluorescent Analogs and Their Use as Tracer Labels in Clinical and Biological Applications," II. Experimental Characterization, *Analytical Biochemisty*, vol. 262, pp. 157-176 (1998) U.S.

Brada, et al., "Golden Blot"—Detection of Polyclonal and Monoclonal Antibodies Bound to Antigens on Nitrocellulose by Protein A-Gold Complexes, *Analytical Biochemistry*, vol. 42, pp. 79-83 (1984) U.S.

Dunn, et al., A Novel Method to Map Transcripts: Evidence for homology between an Adenovirus mRNA and Discrete Multiple Regions of the Viral Genome, *Cell*, vol. 12, pp. 23-36, (1997) U.S.

Hacker, High performance—Nanogold—Silver in situ hybridisation, *Eur. J. Histochem*, vol. 42, pp. 111-120 (1998) U.S.

Ranki, et al., "Sandwich hybridization as a convenient method for the detection of nucleic acids in crude samples," *Gene*, vol. 21, pp. 77-85 (1983) U.S.

Romano, et al., "An antiglobulin reagent labelled with colloidal gold for use in electron microscopy," *Immunochemistry*, vol. 11, pp. 521-522 (1974) Great Britain.

O.D. Velev, et al., "In Situ Assembly of Collordal Particles into MIniaturized Biosensors," *Langmuir*, vol. 15, No. 11, pp. 3693-3698, May 25, 1999.

Borman, *Chem.Eng. News*, Dec. 8, 1996, pp. 42-43 (1996).

Tomlinson et al., *Anal. Biochem*, vol. 171, pp. 217-222 (1998).

Alivisatos et al., "Organization of 'nanocrystal molecules' using DNA," *Nature*, vol. 382, pp. 609-611 (1996).

Bain, et al., "Modeling Oragnic Surfaces with Self-Assembled Monolayers," *Angew. Chem. Int. Ed. Engl.*, vol. 28, pp. 506-512 (1989).

Bradley, "The Chemistry of Transition Metal Colloids," *Clusters and Colloids: From Theory to Applications*, G. Schmid, Editor BCH, Weinheim, New York, pp. 459-542 (1994).

Brust et al., "Novel Gold-Dithiol Nano-Networks with Non-Metallic Electronic Properties," *Adv. Mater.*, vol. 7, pp. 795-797 (1995).

Chen et al., "A Specific Quandrilateral Synthesized from DNA Branched Junctions," *J. Am. Chem. Soc.*, vol. 111, pp. 6402-6407 (1989).

Chen & Seeman, "Synthesis from DNA of a molecule with a connectivity of a cube," *Nature*, vol. 350 pp. 631-633 (1991).

Chen et al., Crystal Structure of a Four-Stranded Intercalated DNA: $d(C_4)^{\dagger\ddagger}$ *Biochem.*, vol. 33, pp. 13540-13546 (1994).

Dagani, "Supramolecular Assemblies DNA to organize gold nanoparticles," *Chemical & Engineering News*, p. 6-7, Aug. 19, 1996.

Dubois & Nuzzo, "Synthesis, Structure, and Properties of Model Organic Surfaces," *Annu. Rev. Phys. Chem.*, vol. 43, pp. 437-464 (1992).

Elghanian et al., "Selective Colorimetric Detection of Polynucleotides Based on the Distance-Dependent Optical Properties of Gold Nanoparticles," *Science*, vol. 277, pp. 1078-1081 (1997).

Grabar et al., "Prepartion and Characterization of Au Colloid Monolayers," *Anal. Chem.* vol. 67, pp. 735-743 (1995).

Hacia et al.,"Detection of heterozygous mutations in BRCA1 using high density oligonucleotide arrays and two-colour florescence analysis," *Nature Genet.*, vol. 14, pp. 441-447 (1996).

Jacoby, "Nanoparticles change color on binding to nucleotide target," *Chemical &Engineering News*, p. 10, Aug. 25, 1997.
Letsinger et al., Use of Hydrophobic Substituents in Controlling Self-Assemby of Oligonucleotides, *J. Am. Chem. Soc.*, vol. 115, pp. 7535-7536 (1993).
Letsinger et al., "Control of Excimer Emission and Photochemsity of Stilbene Units Oligonucleotide Hybridization," *J. Am. Chem. Soc.*, vol. 116, pp. 811-812 (1994).
Marsh et al., "A new DNA nanostructure, the G-wire, imaged by scanning probe microscopy," *Nucleic Acids Res.*, vol. 23, pp. 696-700 (1995).
Nirkin, "H-DNA and Related Structures," *Annu. Review Biophys. Biomol. Struct.*, vol. 23, pp. 541-576 (1994).
Mirkin et al., "A DNA-based method for rationally assembling nanoparticles into macroscopic materials," *Nature*, vol. 382, pp. 607-609 (1996).
Mirkin et al., "DNA-Induced Assembly of Gold Nanoparticles: A Method for Rationally Organizing Colloidal Particles into Ordered Macroscopic Materials," *Abstract* 249, Abstracts of Papers Part 1, 212 ACS National Meeting 0-8412-3402-7, American Chemical Society, Orlando, FL, Aug. 25-29, 1996.
Mucic et al., "Synthesis and characterizations of DNA with ferrocenyl groups attached to their 5'-termini: electrochemical characterization of a redox-active nucleotide monolayer," *Chem. Commun.*, pp. 555-557 (1996).
Mulvaney, "Surface Plasmon Spectoscopy of Nanosized Metal Particles," *Langmuir*, vol. 12, pp. 788-800 (1996).
Rabke-Clemmer et al., "Analysis of Functionalized DNA Adsorption on Au(111) Using Electron Spectroscopy," *Langmuir*, vol. 10, pp. 1796-1800 (1994).
Roubi, "Molecular Machines—Nanodevice with rotating arms assembled from synthetic DNA," *Chemical & Engineering News*, p. 13, (Jan. 1999).
Seeman et al., "Synthetic DNA knots and catenanes," *New J. Chem.*, vol. 17, pp. 739-755 (1993).
Shaw & Wang, "Knotting of a DNA Chain During Ring Closure," *Science*, vol. 260, pp. 533-536 (1993).
Shekhtman et al., "Sterostructure of replicative DNA catenanes from eukaryotic cells," *New J. Chem.* vol. 17, pp. 757-763 (1993).
Smith and Feigon, "Quadruplex structure of *Oxytricha telomeric* DNA oligonucleotides," *Nature*, vol. 356, pp. 164-168 (1992).
Thein et al., "The use of synthetic oligonucleotides as specific hybridization probes in the diagnosis of genetic disorders," 2nd Ed., K.E. Davies, Ed., Oxford University Press, Oxford, New York, Tokyo, p. 21-33 (1993).
Wang et al., "Assembly and Characterization of Five-Arm and Six-Arm DNA Brached Junctions," *Biochem.*, vol. 30, pp. 5667-5674 (1991).
Wang et al., "A DNA Aptamer Which Binds to and Inhibits Thrombin Exhibits a New Strucural Motif for DNA," *Biochem.*, vol. 32, pp. 1899-1904 (1993).
Weisbecker et al., "Molecular Self-Assembly of Aliphatic Thiols on Gold Colloids," *Langmuir*, vol. 12, pp. 3763-3772 (1996).
Wells, "Unusual DNA Structures," *J. Biol. Chem.*, vol. 263, pp. 1095-1098 (1988).
Zhang et al., "Information Liposomes: Complexes Derived from Cholesteryl-conjugated Oligonucleotides and Liposomes," *Tetrahedron Lett.*, vol. 37, pp. 6243-6246 (1996).
Ahmadi, T.S. et al., *Science*, vol. 272, pp. 1924-1926 (1996).
Allara and Nuzzo, *Langmuir*, vol. 1, pp. 45-52 (1985).
Bahnemann, in *Photochemical Conversion and Storage of Solar Energy* (eds. Pelizetti and Schiavello 1991), pp. 251-276.
Brus, *Appl. Phys. A.*, vol. 53, pp. 465-474 (1991).
Burwell, *Chemical Technology*, vol. 4, pp. 370-377 (1974).
Eltekova and Eltekov, *Langmuir*, vol. 3, pp. 951-957 (1987).
Frens, *Nature Phys. Sci.*, vol. 241, pp. 20-22 (1973).
Henglein, *Top. Curr. Chem.*, vol. 143, pp. 113-181 (1988).
Henglein, *Chem. Rev.*, vol. 89, pp. 1861-1873 (1989).
Henglein, A. et al., *J. Phys. Chem.*, vol. 99, pp. 14129-14136 (1995).
Hickman et al., *J. Am. Chem. Soc.*, vol. 111, pp. 7271-7272 (1989).
Hubbard, *Acc. Chem. Res.*, vol. 13, pp. 177-184 (1980).
Lee et al., *J. Phys. Chem.*, vol. 92, pp. 2597-2601 (1998).
Maoz and Sagiv, *Langmuir*, vol. 3, pp. 1034-1044 (1987).

Maoz and Sagiv, *Langmuir*, vol. 3, pp. 1045-1051 (1987).
Letsinger, R., et al., "Chemistry of Oligonucleotide-Gold Nanoparticle Conjugates," *Phosphorus, Sulfur and Silicon*, vol. 144, p. 359-362 (1999).
Letsinger, R., et al., "Use of a Steroid Cyclic Disulfide Anchor in Constructing Gold Nanoparticle—Oligonucleotide Conjugates," *Bioconjugate Chem*, p. 289-291 (2000).
Li Z., et al., "Multiple thiol-anchor capped DNA-gold nanoparticle conjugates," *Nucleic Acids Research*, vol. 30, p. 1558-1562 (2002).
Nuzzo R., et al., "Spontaneously Organized Molecular Assemblies. 3. Preparation and Properties of Solution Adsorbed Monolayers of Organic Disulfides on Gold Surfaces," *J. Am Chem. Soc.*, vol. 109, p. 2358-2368 (1987).
Otsuka, H., et al., "Quantitative and Reversible Lectin-Induced Association of Gold Nanoparticles Modified with $\alpha$-Lactosyol-$\omega$-mercapto-poly(ethyleneglycol)," *J. Am Chem. Soc.*, vol. 123, p. 8226-8230 (2001).
Wuelfing, P., et al., "Nanometer Gold Clusters Protected by Surface-Bound Monolayers of Tiolated Poly(ethylene glycol) Polymer Electrolyte," *J. Am Chem. Soc.*, vol. 120, p. 12696-12697 (1998).
Bassel, et al, *J. Cell. Biol.*, vol. 126, No. 4, pp. 863-876 (1994).
Braun et al., *Nature*, vol. 391, pp. 775-778 (1998).
Braun-Howland et al., *Biotechniques*, vol. 13, No. 6, pp. 928-933 (1992).
Chrisey et al., *Nucleic Acids Res.*, vol. 24, No. 15, pp. 3040-3047 (1996).
Curtis, A.C., et al., *Angew. Chem. Int. Ed. Engl.*, vol. 27, No. 11, pp. 1530-1533 (1988).
Hegner et al., *FEBS Lett.*, vol. 226, No. 3, pp. 452-456 (1993).
Iler, *The Chemistry of Silica*, Chapter 6, pp. 622-729 (Wiley 1979).
Zimmerman and Cos, *Nucleic Acids Res.*, vol. 22, No. 3, pp. 492-497 (1994).
Brown T., et al., "Modern Machine-aided methods of oligodeoxyribonucleotide synthesis", *Oligonucleotides and Analogues: a practical approach* (Ed.: F. Eckstein), Oxford University Press, New York, (1991).
Butler, J. E., "Enzyme-Linked Immunosorbent Assay," *Journal of Immunoassay*, vol. 21(2 & 3), 165-209 (2000).
Chrisey L.A., et al., "Covalent attachement of snythetic DNA to self-assembled monolayer films," *Nucleic Acids Research*, vol. 24, p. 3031-3039 (1996).
Demers L.M., et al, "A fluorescence-based method for determining the surface coverage and hybridization efficiency of thiol-capped oligonucleotides bound to gold thin films and nanoparticles," *Analytical Chemistry*, vol. 72, p. 5535-5541 (2000).
Djksma, M., et al., "Development of an electrochemical immunosensor for direct detection of interferon-gamma at the attomolar level," *Analytical Chemistry*, vol. 73, p. 901-907 (2001).
Eshhar Z., et al., "Generation of hybridomas secreting murine reaginic antibodies of anit-DNP specificity," *Journal of Immunology*, vol. 124, p. 775-780 (1980).
Ferguson, J.A., et al., "High-density fiber optic DNA random microsphere array," *Analytical Chemistry*, vol. 72, p. 5618-5624 (2000).
Fields S, et al., "A novel genetic system to detect protein-protein interactions," *Nature*, vol. 340, p. 245-246 (1989).
Han, M., "Quantum-dot-tagged micropads for multiplexed optical coding of biomolecules," *Nature Biotechnology*, vol. 19, p. 631-635 (2001).
Herbrink P., et al., "ELISA Techniques: New Developments and Practical Applications in a Broad Field" *Techniques in Diagnostic Pathology*, vol. 2, p. 1-19 (1991).
Hergenrother P. J., et al., "Small-Molecule Microarrays: Covalent Attachment and Screening of Alcohol-Containing Small Molecules on Glass Slides," *Journal of the American Chemical Society*, vol. 122, p. 7849-7850 (2000).
MacBeath G., et al., "Printing small molecules as microarrays and detecting protein-ligand interactions en masse," *Journal of the American Chemical Society*, vol. 121, p. 7967-7968 (1999).
Mirkin C. A., et al., "A DNA-based method for rationally assembling nanoparticles into macroscopic materials," *Nature*, vol. 382, p. 607-609 (1996).

Mucic R.C., et al., "DNA-Directed synthesis of binary nanoparticle network materials," *Journal of the American Chemical Society*, vol. 120, p. 12674-12675 (1998).

Nicewarner-Pena, "Submicrometer metallic barcodes," *Science*, vol. 294, 137 (2001).

Pandey A., et al., "Proteomics to study genes and genomes," *Nature*, vol. 405, p. 837-846 (2000).

Park, S.J., et al., "The electrical properties of gold nanoparticles assemblies linked by DNA," *Angewandte Chemie International Edition in English*, vol. 39, p. 3845-3848 (2000).

Park S.J., et al., "Directed Assembly of Periodic Materials from Protein and Oligonucleotde-Modified Nanoparticle Building Blocks," *Angewandte Chemie International Edition in English*, vol. 40, p. 2909-2912 (2001).

Service R. F., "Proteomics, c Can Celera do it again?," *Science*, , vol. 287, p. 2136-2138 (2000).

Storhoff J. J., et al., "One-pot colorimetric differentation of polynucleotides with single base imperfections using gold nanoparticle probes," *Journal of the American Chemical Society*, vol. 120, p. 1959-1964 (1998).

Stohoff J. J., et al., "Programmed Materials Synthesis with DNA," *Chemical Reviews*, vol. 99, p. 1849-1862 (1999).

Taton T. A., et al., "Scanometric DNA array detection with nanoparticle probes," *Science*, vol. 289, p. 1757-1760 (2000).

Wilcheck M., et al., "The avidin-biotin complex in immunology," *Immunology Today*, vol. 5, p. 39-43 (1984).

Winssinger N., et al, "From split-pool library spatially addressable microarrays and its application to functional proteomic profiling," *Agnewandte Chemmie International Edition*, vol. 40, p. 3152-3155 (2001).

Zola H., *Monoclonal Antibodies*, Springer-Verlag, New York, 2000, p. 1-5.

Mohanty J., et al., "Pulsed laser excitation of phosphate stabilized silver nanoparticles." *Proc. Indian Acd. Sci.*, vol. 112, No. 1, p. 63-72, 2000.

Peña-Nicewarner S., et al., "Hybridization and Enzymatic Extension of Au Nanoparticle-Bound Oligonucleotides," *J. Am. Chem. Soc.*, vol. 124, p. 7314-7323 (2002).

Whitesides G.M., et al., "Soft Lithography in Biology and Biochemistry," *Annu. Rev. Biomed. Eng.*, p. 335-373 (2001).

Massart, R., *IEEE Transactions on Magnetics*, vol. 17, pp. 1247-1248 (1981).

Matteucci and Caruthers, *J. Am. Chem. Soc.*, vol. 103, pp. 3185-3191, 1981.

Olshavsky et al., *J. Am. Chem. Soc.*, vol. 112, pp. 9438-9439 (1990).

Soriaga and Hubbard, *J. Am. Chem. Soc.*, vol. 104, pp. 3937-3945 (1982).

Timmons and Zisman, *J. Phys. Chem.*, vol. 69, pp. 984-990 (1965).

Tompkins and Allara, *J. Colloid Interface Sci.*, vol. 49, pp. 410-421 (1974).

Uchida et al., *J. Phys. Chem.*, vol. 95, pp. 5382-5384 (1992).

Wang and Herron, *J. Phys. Chem.*, vol. 95, pp. 525-532 (1991).

Wasserman et al., *Langmuir*, vol. 5, pp. 1074-1087 (1989).

Weller, *Angew. Chem. Int. Ed. Engl.*, vol. 32, pp. 41-53 (1993).

Whitesides, *Proceedings of the Robert A. Welch Foundation 39th Conference on Chemical Research Nanophase Chemistry*, Houston, TX, pp. 109-121 (1995).

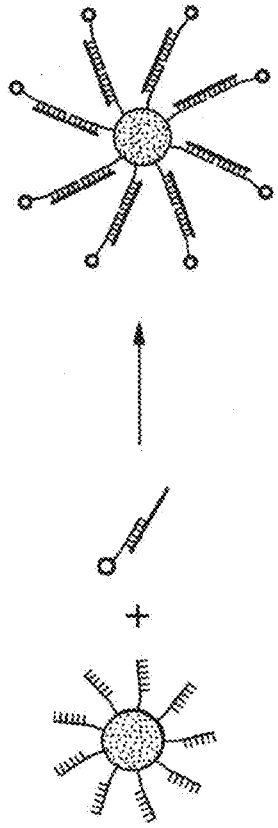
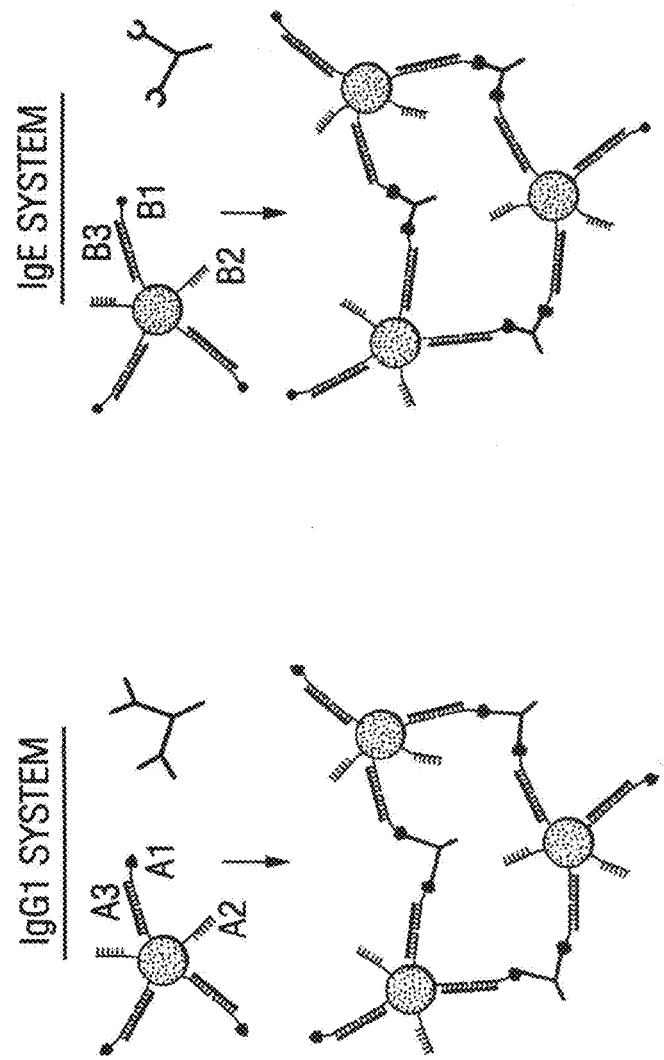
FIG. 1A
FIG. 1B

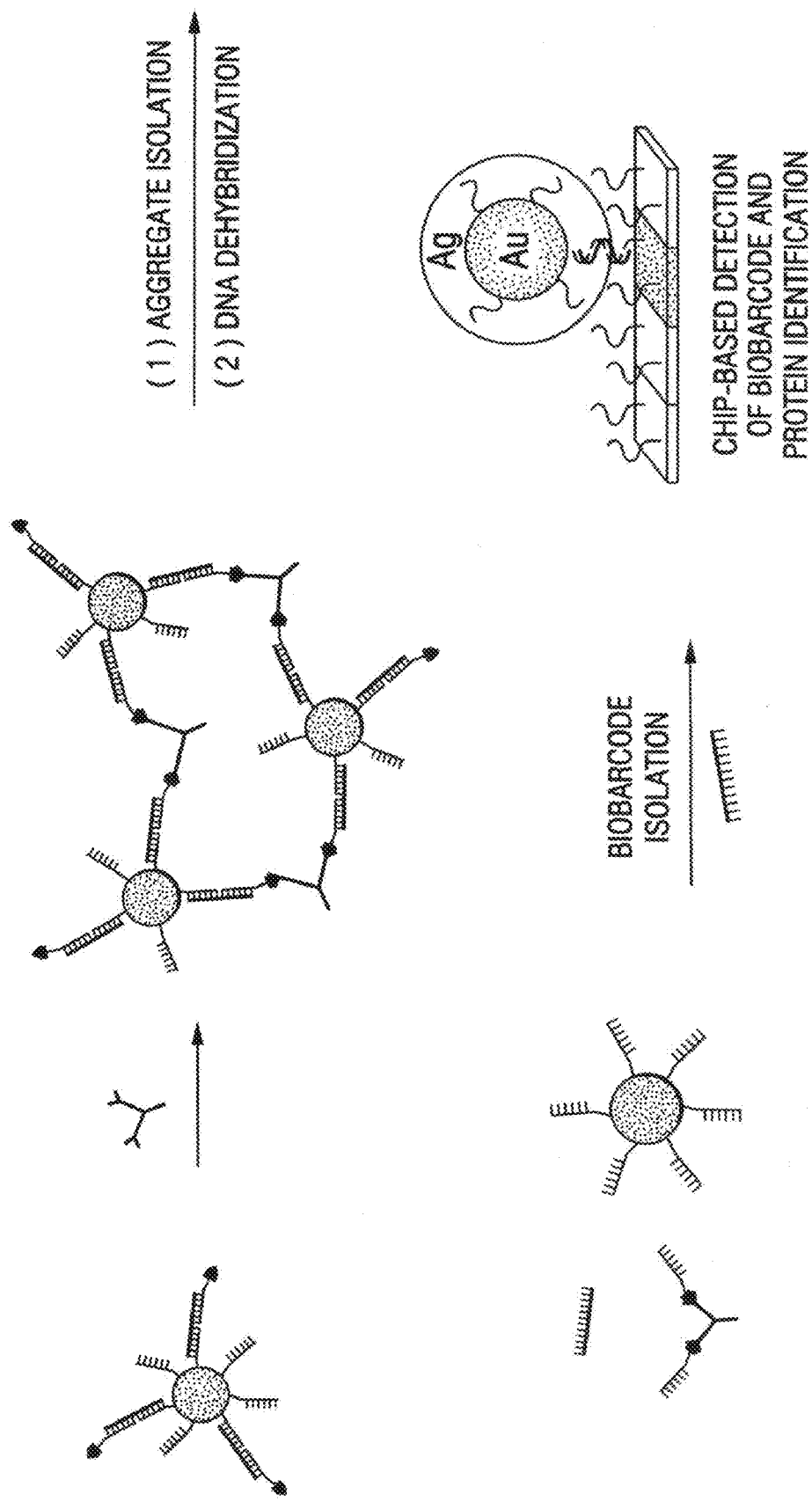

BIO-BARCODES BASED ON OLIGONUCLEOTIDE-MODIFIED PARTICLES

CROSS-REFERENCE

This application is a continuation-in-part of U.S. patent application Ser. No. 09/820,279, filed Mar. 28, 2001, now U.S. Pat. No. 6,750,016, and claims the benefit of U.S. Provisional application Nos. 60/192,699, filed Mar. 28, 2000; and 60/350,560, filed Nov. 13, 2001, which are incorporated by reference in their entirety. The work reported in this application is funded, in part, by NSF, ARO, and NIH grants. Accordingly, the U.S. government has certain rights to the invention described in this application.

FIELD OF THE INVENTION

The present invention relates to a screening method for detecting for the presence or absence of one or more proteins, e.g., antibodies, in a sample. In particular, the present invention relates to a method that utilizes reporter oligonucleotides as biochemical barcodes for detecting multiple protein structures in one solution.

BACKGROUND OF THE INVENTION

The detection of proteins is important for both molecular biology research and medical applications. Diagnostic methods based on fluorescence, mass spectroscopy, gell electrophoresis, laser scanning and electrochemistry are now available for identifying a variety of protein structures. [1-4] Antibody-based reactions are widely used to identify the genetic protein variants of blood cells, diagnose diseases, localize molecular probes in tissue, and purify molecules or effect separation processes.[5] For medical diagnostic applications (e.g. malaria and HIV), antibody tests such as the enzyme-linked immunosorbent assay, Western blotting, and indirect fluorescent antibody tests are extremely useful for identifying single target protein structures. [6,7] Rapid and simultaneous sample screening for the presence of multiple antibodies would be beneficial in both research and clinical applications. However, it is difficult, expensive, and time-consuming to simultaneously detect several protein structures in one solution under homogeneous assay conditions using the aforementioned related protocols.

SUMMARY OF THE INVENTION

The present invention relates to methods, compositions, and kits that utilizes oligonucleotides as biochemical barcodes for detecting multiple protein structures in one solution. The approach takes advantage of protein recognition elements functionalized with oligonucleotide strands and the previous observation that hybridization events that result in the aggregation of gold nanoparticles can significantly alter their physical properties (e.g. optical, electrical, mechanical) .[8-12] The general idea is that each protein recognition element can be encoded with a different oligonucleotide sequence with discrete and tailorable hybridization and melting properties and a physical signature associated with the nanoparticles that changes upon melting to decode a series of analytes in a multi-analyte assay.

In one embodiment of the invention, a method is provided for detecting for the presence of a target analyte in a sample comprising:

providing a particle complex probe comprising a particle having oligonucleotides bound thereto, a DNA barcode, and a oligonucleotide having bound thereto a specific binding complement to a target analyte, wherein the DNA barcode has a sequence having at least two portions, at least some of the oligonucleotides attached to the particle have a sequence that is complementary to a first portion of a DNA barcode, the oligonucleotides having bound thereto a specific binding complement have a sequence that is complementary to a second portion of a DNA barcode, and wherein the DNA barcode is hybridized at least to some of the oligonucleotides attached to the particle and to the oligonucleotides having bound thereto the specific binding complement;

contacting the sample with a particle complex probe under conditions effective to allow specific binding interactions between the analyte and the particle complex probe and to form an aggregated complex in the presence of analyte; and observing whether aggregate formation occurred.

In the presence of target analyte, aggregates are produced as a result of the binding interactions between the particle complex probe and the target analyte. The aggregates may be detected by any suitable means.

In another embodiment of the invention, a method is provided for detecting for the presence of one or more target analytes in a sample comprising:

providing one or more types of particle complex probe comprising a particle having oligonucleotides bound thereto, a DNA barcode, and a oligonucleotide having bound thereto a specific binding complement to a specific target analyte, wherein (i) the DNA barcode has a sequence having at least two portions, (ii) at least some of the oligonucleotides attached to the particle have a sequence that is complementary to a first portion of a DNA barcode, (iii) the oligonucleotides having bound thereto a specific binding complement have a sequence that is complementary to a second portion of a DNA barcode, and (iv) the DNA barcode in each type of particle complex probe has a sequence that is different and that serves as an identifier for a particular target analyte;

contacting the sample with a particle complex probe under conditions effective to allow specific binding interactions between the analyte and the particle complex probe and to form an aggregated complex in the presence of analyte;

isolating aggregated complexes; and analyzing the aggregated complexes to determine the presence of one or more DNA barcodes having different sequences.

Each type of particle complex probe contains a predetermined reporter oligonucleotde or barcode for a particular target analyte. In the presence of target analyte, nanoparticle aggregates are produced as a result of the binding interactions between the nanoparticle complex and the target analyte. These aggregates can be isolated and analyzed by any suitable means, e.g., thermal denaturation, to detect the presence of one or more different types of reporter oligonucleotides.

In yet another embodiment of the invention, a method is provided for detecting for the presence of a target analyte in a sample comprising:

providing a particle complex probe comprising a particle having oligonucleotides bound thereto, a DNA barcode, and a oligonucleotide having bound thereto a specific binding complement to a target analyte, wherein the DNA barcode has a sequence having at least two portions, at least some of the oligonucleotides attached to the particle have a sequence that is complementary to a first portion of a DNA barcode, the oligonucleotides having bound thereto a specific binding complement have a sequence that is complementary to a second portion of a DNA barcode, and wherein the DNA barcode is hybridized at least to some of the oligonucleotides attached to the particle and to the oligonucleotides having bound thereto the specific binding complement;

contacting the sample with a particle complex probe under conditions effective to allow specific binding interactions between the analyte and the particle complex probe and to form an aggregated complex in the presence of analyte;

isolating the aggregated complex and subjecting the aggregated complex to conditions effective to dehybridize the aggregated complex and to release the DNA barcode;

isolating the DNA barcode; and detecting for the presence of DNA barcode.

In the presence of target analyte, nanoparticle aggregates are produced as a result of the binding interactions between the nanoparticle complex and the target analyte. These aggregates are isolated and subject to conditions effective to dehybridize the aggregate and to release the reporter oligonucleotide. The reporter oligonucleotide is then isolated. If desired, the reporter oligonucleotide may be amplified by any suitable means including PCR amplification. Analyte detection occurs indirectly by ascertaining for the presence of reporter oligonucleotide or biobarcode by any suitable means such as a DNA chip.

In yet another embodiment of the invention, a method for detecting for the presence of one or more target analytes in a sample comprising:

providing one or more types of particle complex probe comprising a particle having oligonucleotides bound thereto, a DNA barcode, and a oligonucleotide having bound thereto a specific binding complement to a specific target analyte, wherein (i) the DNA barcode has a sequence having at least two portions, (ii) at least some of the oligonucleotides attached to the particle have a sequence that is complementary to a first portion of a DNA barcode, (iii) the oligonucleotides having bound thereto a specific binding complement have a sequence that is complementary to a second portion of a DNA barcode, and (iv) the DNA barcode in each type of particle complex probe has a sequence that is different and that serves as an identifier for a particular target analyte;

contacting the sample with a particle complex probe under conditions effective to allow specific binding interactions between the analyte and the particle complex probe and to form aggregated complexes in the presence of one or more analytes;

isolating the aggregated complexes and subjecting the aggregated complexes to conditions effective to dehybridize the aggregated complexes and to release the DNA barcodes;

isolating the DNA barcodes; and detecting for the presence of one or more DNA barcodes having different sequences, wherein the identification of a particular DNA barcode is indicative of the presence of a specific target analyte in the sample.

In the presence of one or more target analyte, aggregates are produced as a result of the binding interactions between the particle complex probe and the target analyte. These aggregates are isolated and subject to conditions effective to dehybridize the aggregate and to release the reporter oligonucleotides. The reporter oligonucleotides is then isolated. If desired, the reporter oligonucleotide may be amplified by any suitable means including PCR amplification. Analyte detection occurs indirectly by ascertaining for the presence of reporter oligonucleotide or biobarcode by any suitable means such as a DNA chip.

In yet another embodiment of the invention, a method for detecting for the presence of one or more antibodies in a sample comprising:

providing one or more types of particle complex probe comprising a particle having oligonucleotides bound thereto, a DNA barcode, and a oligonucleotide having bound thereto a hapten to a specific target antibody, wherein (i) the DNA barcode has a sequence having at least two portions, (ii) at least some of the oligonucleotides attached to the particle have a sequence that is complementary to a first portion of a DNA barcode, (iii) the oligonucleotides having bound thereto a hapten to a specific target antibody have a sequence that is complementary to a second portion of a DNA barcode, and (iv) the DNA barcode in each type of particle complex probe has a sequence that is different and that serves as an identifier for a particular target antibody;

contacting the sample with a particle complex probe under conditions effective to allow specific binding interactions between the antibody and the particle complex probe and to form aggregated complexes in the presence of one or more target antibodies;

isolating the aggregated complexes and subjecting the aggregated complexes to conditions effective to dehybridize the aggregated complexes and to release the DNA barcodes;

isolating the DNA barcodes; and detecting for the presence of one or more DNA barcodes having different sequences, wherein the identification of a particular DNA barcode is indicative of the presence of a specific target antibody.

The invention also provides a method is provided for detecting for the presence of a target analyte in a sample which entails generating a particle complex probe in situ. In one embodiment of the invention, a method for detecting for the presence of target analytes comprises:

providing particles having oligonucleotides bound thereto, DNA barcodes, and oligonucleotides having bound thereto a specific binding complement to a target analyte, wherein the DNA barcodes have a sequence with at least two portions, at least some of the oligonucleotides attached to the particles have a sequence that is complementary to a first portion of a DNA barcode, the oligonucleotides having bound thereto a specific binding complement have a sequence that is complementary to a second portion of a DNA barcodes contacting the sample with a particle complex probe under conditions effective to allow hybridization of the DNA barcode to at least to some of the oligonucleotides attached to the particle and to the oligonucleotides having bound thereto the specific binding complement and to allow specific binding interactions between the analyte and the oligonucleotides having bound thereto a specific binding complement to the analyte, said contacting resulting in the formation of an aggregated complex in the presence of analyte; and observing whether aggregate formation occurred.

In another embodiment of the invention, a method is provided for detecting for the presence of one or more target analytes in a sample comprising:

providing one or more types of particles having oligonucleotides bound thereto, one or more types of DNA barcodes, and one or more types of oligonucleotides having bound thereto a specific binding complement to a specific target analyte, wherein (i) each type of DNA barcode has a sequence having at least two portions, (ii) at least some of the oligonucleotides attached to the particle have a sequence that is complementary to a first portion of one or more types of DNA barcode, (iii) each type of oligonucleotide having bound thereto a specific binding complement have a sequence that is complementary to a second portion of a type of DNA barcode, and (iv) each type of DNA barcode serves as an identifier for a particular target analyte and has a sequence that is different from another type of DNA barcode;

contacting the sample with one or more types of particles having oligonucleotides bound thereto, one or more types of DNA barcodes, and one or more types of oligonucleotides having bound thereto a specific binding complement to a specific target analyte, under conditions effective to allow hybridization of each type of DNA barcodes at least to some of the oligonucleotides attached to the particles and to a type of oligonucleotides having bound thereto the specific binding complement and to allow specific binding interactions between a specific target analyte and a type of oligonucleotides having bound thereto a specific binding complement to the specific target analyte, said contacting resulting in the formation of aggregated complexes in the presence of one or more specific target analytes;

isolating aggregated complexes; and analyzing the aggregated complexes to determine the presence of one or more DNA barcode, where the presence of a particular DNA barcode is indicative of the presence of a specific target analyte in the sample.

In yet another embodiment of the invention, a method is provided for detecting for the presence of a target analyte in a sample comprising:

providing particles having oligonucleotides bound thereto, DNA barcodes, and oligonucleotides having bound thereto a specific binding complement to a target analyte, wherein the DNA barcodes have a sequence with at least two portions, at least some of the oligonucleotides attached to the particles have a sequence that is complementary to a first portion of a DNA barcode, the oligonucleotides having bound thereto a specific binding complement have a sequence that is complementary to a second portion of a DNA barcodes;

contacting the sample with a particle complex probe under conditions effective to allow hybridization of the DNA barcode to at least to some of the oligonucleotides attached to the particle and to the oligonucleotides having bound thereto the specific binding complement and to allow specific binding interactions between the analyte and the oligonucleotides having bound thereto a specific binding complement to the analyte, said contacting resulting in the formation of an aggregated complex in the presence of analyte;

isolating the aggregated complex and subjecting the aggregated complex to conditions effective to dehybridize the aggregated complex and to release the DNA barcode;

isolating the DNA barcode; and detecting for the presence of DNA barcode.

In yet another embodiment of the invention, a method is provided for detecting for the presence of one or more target analytes in a sample comprising:

providing one or more types of particles having oligonucleotides bound thereto, one or more types of DNA barcodes, and one or more types of oligonucleotides having bound thereto a specific binding complement to a specific target analyte, wherein (i) each type of DNA barcode has a sequence having at least two portions, (ii) at least some of the oligonucleotides attached to the particle have a sequence that is complementary to a first portion of one or more types of DNA barcode, (iii) each type of oligonucleotide having bound thereto a specific binding complement have a sequence that is complementary to a second portion of a type of DNA barcode, and (iv) each type of DNA barcode serves as an identifier for a particular target analyte and has a sequence that is different from another type of DNA barcode;

contacting the sample with one or more types of particles having oligonucleotides bound thereto, one or more types of DNA barcodes, and one or more types of oligonucleotides having bound thereto a specific binding complement to a specific target analyte, under conditions effective to allow hybridization of each type of DNA barcodes at least to some of the oligonucleotides attached to the particles and to a type of oligonucleotides having bound thereto the specific binding complement and to allow specific binding interactions between a specific target analyte and a type of oligonucleotides having bound thereto a specific binding complement to the specific target analyte, said contacting resulting in the formation of aggregated complexes in the presence of one or more specific target analytes;

isolating the aggregated complexes and subjecting the aggregated complexes to conditions effective to dehybridize the aggregated complexes and to release the DNA barcodes;

isolating the DNA barcodes; and detecting for the presence of one or more DNA barcodes having different sequences, wherein the identification of a particular DNA barcode is indicative of the presence of a specific target analyte.

In yet another embodiment of the invention, a method is provided for detecting for the presence of one or more antibodies in a sample comprising:

providing one or more types of particles having oligonucleotides bound thereto, one or more types of DNA barcodes, and one or more types of oligonucleotides having bound thereto a hapten to a specific antibody, wherein (i) each type of DNA barcode has a sequence having at least two portions, (ii) at least some of the oligonucleotides attached to the particle have a sequence that is complementary to a first portion of one or more types of DNA barcode, (iii) each type of oligonucleotide having bound thereto a hapten to a specific antibody has a sequence that is complementary to a second portion of a type of DNA barcode, and (iv) each type of DNA barcode serves as an identifier for a particular target antibody and has a sequence that is different from another type of DNA barcode;

contacting the sample with one or more types of particles having oligonucleotides bound thereto, one or more types of DNA barcodes, and one or more types of oligonucleotides having bound thereto a hapten to a specific target antibody, under conditions effective to allow hybridization of each type of DNA barcodes at least to some of the oligonucleotides attached to the particles and to a type of oligonucleotides having bound thereto the hapten and to allow specific binding interactions between a specific target antibody and a type of oligonucleotides having bound thereto a hapten to the specific target antibody, said contacting resulting in the formation of aggregated complexes in the presence of one or more specific target antibodies;

isolating the aggregated complexes and subjecting the aggregated complexes to conditions effective to dehybridize the aggregated complexes and to release the DNA barcodes;

isolating the DNA barcodes; and detecting for the presence of one or more DNA barcodes having different sequences, wherein the identification of a particular DNA barcode is indicative of the presence of a specific target antibody.

The invention also provides kits for target analyte detection. In one embodiment of the invention, a kit is provided for detecting a target analyte in a sample, the kit comprising at least one container including particle complex probes comprising a particle having oligonucleotides bound thereto, a DNA barcode, and a oligonucleotide having bound thereto a specific binding complement to a target analyte, wherein the DNA barcode has a sequence having at least two portions, at least some of the oligonucleotides attached to the particle have a sequence that is complementary to a first portion of a DNA barcode, the oligonucleotides having bound thereto a specific binding complement have a sequence that is complementary to a second portion of a DNA barcode, and wherein the DNA barcode is hybridized to at least to some of the oligonucleotides attached to the particle and to the oligonucleotides having bound thereto the specific binding complement, and an optional substrate for observing a detectable change.

In another embodiment of the invention, a kit is provided for detecting one or more target analytes in a sample, the kit comprising at least one or more containers, container holds a type of particle complex probe comprising a particle having oligonucleotides bound thereto, a DNA barcode, and a oligonucleotide having bound thereto a specific binding complement to a specific target analyte, wherein (i) the DNA barcode has a sequence having at least two portions, (ii) at least some of the oligonucleotides attached to the particle have a sequence that is complementary to a first portion of a DNA barcode, (iii) the oligonucleotides having bound thereto a specific binding complement have a sequence that is complementary to a second portion of a DNA barcode, and (iv) the DNA barcode in each type of particle complex probe has a sequence that is different and that serves as an identifier for a particular target analyte; wherein the kit optionally includes a substrate for observing a detectable change.

In yet another embodiment of the invention, a kit is provided for the detection of a target analyte, the kit includes at least one pair of containers and an optional substrate for observing a detectable change, the first container of the pair includes particle probe comprising a particle having oligonucleotides bound thereto and a DNA barcode having a sequence of at least two portions, wherein at least some of the oligonucleotides attached to the particle have a sequence that is complementary to a first portion of a DNA barcode;

the second container of the pair includes an oligonucleotide having a sequence that is complementary to a second portion of the DNA barcode, the oligonucleotide having a moiety that can be used to covalently link a specific binding pair complement of a target analyte.

In yet another embodiment of the invention, a kit is provided for the detection of multiple target analytes in a sample, the kit includes at least two or more pairs of containers, the first container of each pair includes particle complex probes having particles having oligonucleotides bound thereto and a DNA barcode having a sequence of at least two portions, wherein at least some of the oligonucleotides bound to the particles have a sequence that is complementary to a first portion of a DNA barcode having at least two portions; and the second container of each pair contains a oligonucleotide having a sequence that is complementary to a second portion of the DNA barcode, the oligonucleotide having a moiety that can be used to covalently link a specific binding pair complement of a target analyte, wherein the DNA barcode for type of particle complex probe has a sequence that is different and that serves as an identifer for a target analyte and wherein the kit optionally include a substrate for observing a detectable change.

In yet another embodiment of the invention, a kit is provided for the detection of multiple target analytes in a sample, the kit includes a first container and at least two or more pairs of containers, the first container includes particle complex probes having particles having oligonucleotides bound thereto;

the first container of the pair includes a DNA barcode having a sequence of at least two portions, wherein at least some of the oligonucleotides bound to the particles have a sequence that is complementary to a first portion of the DNA barcode; and the second container of each pair contains a oligonucleotide having a sequence that is complementary to a second portion of the DNA barcode, the oligonucleotide having a moiety that can be used to covalently link a specific binding pair complement of a target analyte, wherein the DNA barcode present in the first container of each pair of containers serves as an identifer for a target analyte and has a sequence that is different from a DNA barcode in another pair of containers, and wherein the kite optionally include a substrate for observing a detectable change.

In yet another embodiment of the invention, the particle of any of the foregoing kits may comprise a nanoparticle such as metal, semiconductor, insulator, or magnetic nanoparticles, preferably gold nanoparticles.

The invention also includes a system for detecting one or more target analytes in a sample comprising:

one or more types of particle complex probes, each particle complex probe comprising a particle having oligonucleotides bound thereto, a DNA barcode, and a oligonucleotide having bound thereto a specific binding complement to a specific target analyte, wherein (i) the DNA barcode has a sequence having at least two portions, (ii) at least some of the oligonucleotides attached to the particle have a sequence that is complementary to a first portion of a DNA barcode, (iii) the oligonucleotide having bound thereto a specific binding complement have a sequence that is complementary to a second portion of a DNA barcode, and (iv) the DNA barcode in each type of particle complex probe has a sequence that is different and that serves as an identifier for a particular target analyte.

The particle in the system preferably comprises a nanoparticle such as metal, semiconductor, insulator, or magnetic nanoparticles, preferably gold nanoparticles.

The invention also comprises a particle complex probe comprising a particle having oligonucleotides bound thereto, a DNA barcode, and a oligonucleotide having bound thereto a specific binding complement to a target analyte, wherein the DNA barcode has a sequence having at least two portions, at least some of the oligonucleotides attached to the particle have a sequence that is complementary to a first portion of a DNA barcode, the oligonucleotides having bound thereto a specific binding complement have a sequence that is complementary to a second portion of a DNA barcode, and wherein the DNA barcode is hybridized at least to some of the oligonucleotides attached to the particle and to the oligonucleotides having bound thereto the specific binding complement. The particle in the probe preferably comprises a nanoparticle such as metal, semiconductor, insulator, or magnetic nanoparticles, preferably gold nanoparticles.

The invention also includes an oligonucleotide sequence having bound thereto a specific target complement to a target analyte.

The invention also includes a DNA barcode comprising a oligonucleotide sequence that serves as an identifier for the presence of a specific target analyte.

The invention also includes two or more DNA barcodes comprising an oligonucleotide sequence, each DNA barcode having a different oligonucleotide sequence and serving as an identifier for the presence of a specific target analyte.

As used herein, a "type of" nanoparticles, conjugates, particles, latex microspheres, etc. having oligonucleotides attached thereto refers to a plurality of that item having the same type(s) of oligonucleotides attached to them. "Nanoparticles having oligonucleotides attached thereto" or "Nanoparticles having oligonucleotides attached thereto" are also sometimes referred to as "nanoparticle-oligonucleotide conjugates" or, in the case of the detection methods of the invention, "nanoparticle-oligonucleotide probes," "nanoparticle probes," or just "probes."

The term "nanoparticle complex" or "nanoparticle complex probe" refers to a conjugate comprised of nanoparticle-oligonucleotide conjugates, a reporter oligonucleotide, and an oligonucleotide having bound thereto a specific binding complement to a target analyte.

The term "analyte" refers to the compound or composition to be detected, including drugs, metabolites, pesticides, pollutants, and the like. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The types of proteins, blood clotting factors, protein hormones, antigenic polysaccharides, microorganisms and other pathogens of interest in the present invention are specifically disclosed in U.S. Pat. No. 4,650,770, the disclosure of which is incorporated by reference herein in its entirety.

The monoepitopic ligand analytes will generally be from about 100 to 2,000 molecular weight, more usually from 125 to 1,000 molecular weight.

The analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

The term "specific binding pair (sbp) member" refers to one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

The term "ligand" refers to any organic compound for which a receptor naturally exists or can be prepared. The term ligand also includes ligand analogs, which are modified ligands, usually an organic radical or analyte analog, usually of a molecular weight greater than 100, which can compete with the analogous ligand for a receptor, the modification providing means to join the ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

The term "receptor" or "antiligand" refers to any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, avidin, protein A, barstar, complement component C1q, and the like. Avidin is intended to include egg white avidin and biotin binding proteins from other sources, such as streptavidin.

The term "specific binding" refers to the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

The term "non-specific binding" refers to the non-covalent binding between molecules that is relatively independent of specific surface structures. Non-specific binding may result from several factors including hydrophobic interactions between molecules.

The term "antibody" refers to an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab').sub.2, Fab', and the like. In addition, aggregates, polymers, and conjugates of immunoglobulins or their fragments can be used where appropriate so long as binding affinity for a particular molecule is maintained.

BRIEF DESCRIPTION OF THE FIGURES

FIG. 1 illustrates a DNA/Au nanoparticle-based protein detection scheme. (A) Preparation of hapten-modified nanoparticle probes. (B) Protein detection using protein binding probes. Notice that there are nine G,C pairs in sequence A and there are only two G,C pairs in sequence B.

FIG. 3 illustrates an array-based protein detection scheme using DNA as a biobarcode for the protein.

DETAILED DESCRIPTION OF THE INVENTION

Figure 2A:
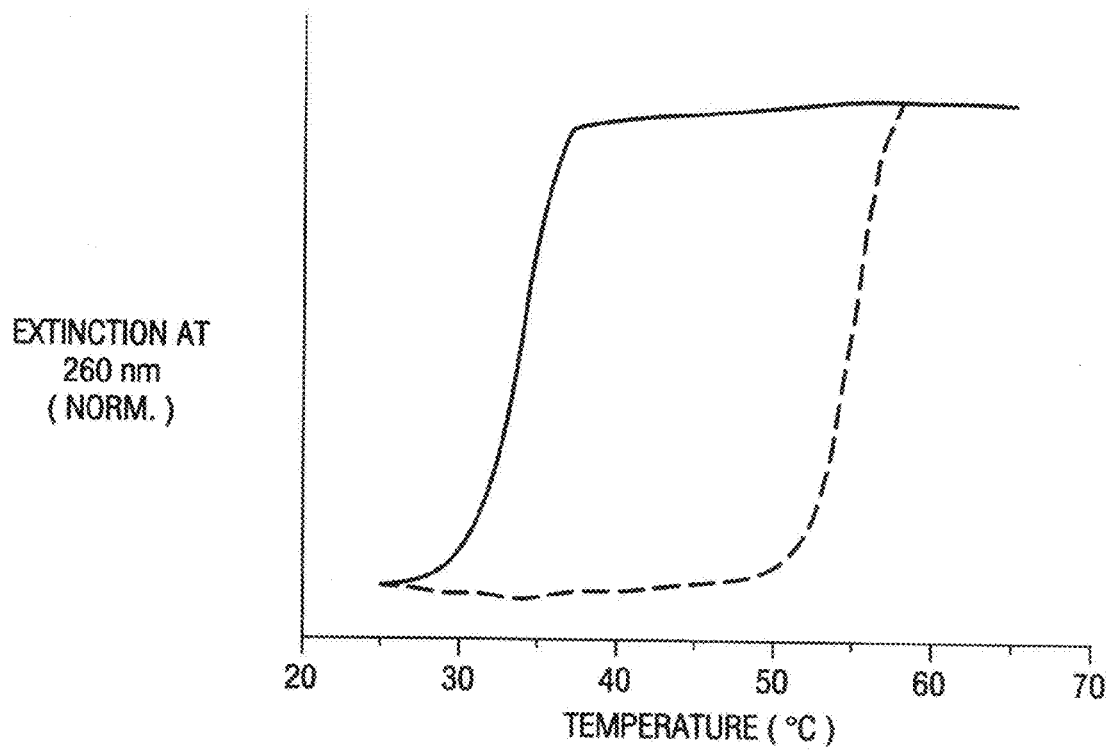
FIG. 2 illustrates thermal denaturation profiles for Au nanoparticle aggregates linked by DNA and proteins. Extinction at 260 nm was monitored as a function of increasing temperature (1° C./min, 1 min holding time). Each UV-Vis spectrum was measured under constant stirring to suspend the aggregates. All the aggregates were suspended in 1 ml of 0.3 M PBS prior to performing the melting analyses. A) Two probes with one target antibody present IgE (——), IgG1 (---)); all data have been normalized; (B) Two probes with both target antibodies present. Inset; first derivative of the thermal denaturation curve.

The present invention relates to a method that utilizes oligonucleotides as biochemical barcodes for detecting multiple protein structures in one solution (FIG. 1). The approach takes advantage of protein recognition elements functionalized with oligonucleotide strands and the previous observation that hybridization events that result in the aggregation of gold nanoparticles can significantly alter their physical properties (e.g. optical, electrical, mechanical).[8-12] The general idea is that each protein recognition element can be encoded with a different oligonucleotide sequence with discrete and tailorable hybridization and melting properties and a physical signature associated with the nanoparticles that changes upon melting to decode a series of analytes in a multi-analyte assay. Therefore, one can use the melting temperature of a DNA-linked aggregate and a physical property associated with the nanoparticles that changes upon melting to decode a series of analytes in a multi-analyte assay. The barcodes herein are different from the ones based on physical diagnostic markers such as nanorods,[23] flourophore-labeled beads,[24] and quantum dots,[25] in that the decoding information is in the form of chemical information stored in a predesigned oligonucleotide sequence.

In one aspect of the invention, a method for detecting for the presence of a target analyte, e.g., an antibody, in a sample is provided. An antibody such as immunoglobulin E (IgE) or immunoglobulin G1 (IgG1) shown in the Examples below can be detected with olignucleotide-modified probes prehybridized with oligonucleotide strands modified with the appropriate hapten (biotin in the case of IgG1 and dinitrophenyl (DNP) in the case of IgE; FIG. 1A).[13,14] The DNA sequences in the proof-of-concept assays presented in the Examples below were designed in a way that would ensure that the two different aggregates formed from the probe reactions with IgG1 and IgE would melt at different temperatures, FIG. 1B. The probes for IgG1 have longer sequences and greater G,C base contents than those for IgE. Therefore, the former sequences melt at a higher temperature than the latter ones. These sequence variations allow one to prepare probes with distinct melting signatures that can be used as codes to identify which targets have reacted with them to form nanoparticle aggregates. Three different systems have been studied: (1) two probes with one target antibody present (IgG1 or IgE); (2) two probes with the two different target antibodies present, and (3) a control where no target antibodies are present.

In this aspect of the invention, a method is provided for detecting the presence of a target analyte, e.g., an antibody, in a sample comprises contacting a nanoparticle probe having oligonucleotides bound thereto with a sample which may contain a target analyte. At least some of the oligonucleotides attached to the nanoparticle are bound to a first portion of a reporter oligonucleotide as a result of hybridization. A second portion of the reporter oligonucleotide is bound, as a result of hybridization, to an oligonucleotide having bound thereto a specific binding complement (e.g., antigen) to the analyte. The contacting takes place under conditions effective to allow specific binding interactions between the analyte and the nanoparticle probe. In the presence of target analyte, nanoparticle aggregates are produced. These aggregates may be detected by any suitable means.

In practicing the invention, a nanoparticle complex probes are prepared by hybridizing the nanoparticles having oligonucleotides bound thereto with an oligonucleotide modified with a specific binding complement to a target analyte, and a reporter oligonucleotide. At least some of the oligonucleotides attached to the nanoparticle have a sequence that is complementary to a first portion of a reporter oligonucleotide. The oligonucleotides having bound thereto a specific binding complement have a sequence that is complementary to a second portion of a reporter oligonucleotide. The reporter oligonucleotide hybridizes to the at least to some of the oligonucleotides attached to the nanoparticle and to the oligonucleotides having bound thereto the specific binding complement, forming the nanoparticle complex probe under conditions sufficient to allow for hybridization between the components. Any suitable solvent medium and hybridization conditions may be employed in preparing the nanoparticle complex solution that allows for sufficient hybridization of the components. Preferably, the components are hybridized in a phosphate buffered solution (PBS) comprised of 0.3 M NaCl and 10 mM phosphate buffer (pH 7) at room temperature for about 2-3 hours. The concentration of nanoparticle-oligonucleotide conjugates in the hybridization mixture range between about 2 and about 50, preferably about 13 nM. The concentration of hapten-modified oligonucleotides generally ranges between about 50 and about 900, preferably about 300 nM. The concentration of reporter oligonucleotide generally ranges between about 50 and about 900, preferably about 300 nM. Unreacted hapten-modified oligonucleotide and reporter oligonucleotides may be optionally, but preferably, removed by any suitable means, preferably via centrifugation (12,000 rpm, 20 minutes) of the hybridization mixture and subsequent decanting of the supernatant. The prepared complexes were stored in 0.3 M NaCl and 10 mM phosphate buffer (pH 7-7.4), 0.01% azide solution at 4-6° C.

A typical assay for detecting the presence of a target analyte, e.g, antibody, in a sample is as follows: a solution containing nanoparticle complex probe comprising nanoparticles having oligonucleotides bound thereto, a reporter oligonucleotide, and an oligonucleotide having a specific binding complement to the target analyte, is admixed with an aqueous sample solution believed to contain target protein. The total protein content in the aqueous sample solution generally ranges between about 5 and about 100, usually about 43 ug/ml. The concentration of nanoparticles in the reaction mixture generally ranges between about 2 and about 20, usually about ~13 nM. The total volume of the resulting mixture generally ranges between about 100 and about 1000, preferably about 400 uL. Any suitable solvent may be employed in preparing the aqueous sample solution believed to contain target analyte, preferably PBS comprising 0.3 M NaCl and 10 mM phosphate buffer (pH 7-7.4).

The resulting assay mixture is then incubated at a temperature ranging between about 35 and about 40° C., preferably at 37° C., for a time ranging between about 30 and about 60, preferably about 50 minutes, sufficient to facilitate specific binding pair, e.g., protein-hapten, complexation. If the target protein is present, particle aggregation takes place effecting a shift in the gold nanoparticle plasmon band and a red-to-purple color change along with precipitation. The hybridized products are centrifuged (e.g., 3000 rpm for 2 minutes), and the supernatant containing unreacted elements are decanted prior to analysis.

If desired, the nanoparticle complex probe may be prepared in situ within the assay mixture by admixing all the nanoparticles having oligonucleotides bound thereto, the reporter oligonucleotide, and the hapten-modified oligonucleotide with the sample suspected of containing a target analyte. To ensure complete hybridization among all the components, especially the complementary DNA strands, the assay mixture may be incubated to expedite hybridization at −15° C. for 20 minutes (Boekel Tropicooler Hot/Cold Block Incubator) and stored at 4° C. for 24 hours. In practicing the invention, however, it is preferred that the nanoparticle complex probe is prepared prior to conducting the assay reaction to increase the amount of DNA barcode within the nanoparticle complex probe.

Figure 2B:
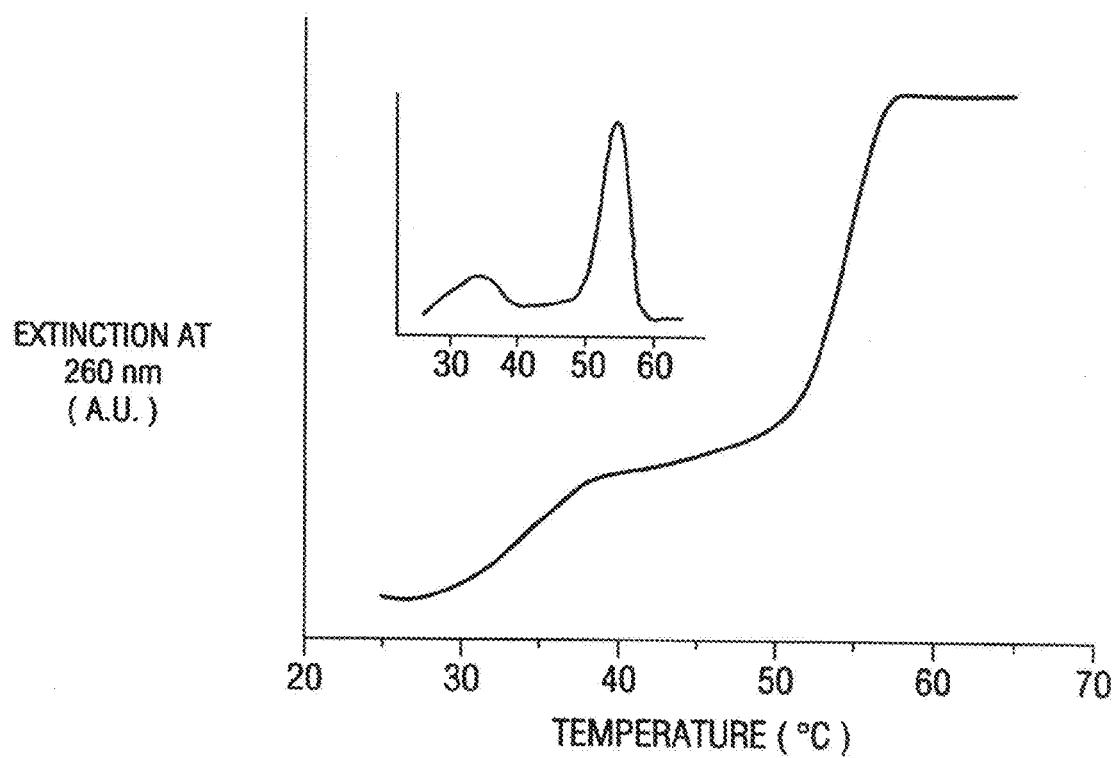

To determine which proteins are present, a melting analysis of the aggregates which monitors the extinction at 260 nm as a function of temperature may carried out in the solution. See, for instance, FIG. 2 in Example 3 which describes analysis of a sample containing one or two known target analytes: IgG1 and IgE. As discussed in Example 3, when IgG1 is treated with the probes via the aforementioned protocol, the solution turns pinkish-blue, indicating the formation of nanoparticle aggregates. In a control experiment where no target but background proteins are present, there is no discernible precipitation. A melting analysis of the solution shows a sharp transition with a melting temperature (Tm) of 55° C. This is the expected transition for the IgG1 target, FIG. 2A (---). If IgE is added to a fresh solution of probes, the same color change is observed but the melting analysis provides a curve with a Tm of 36° C., the expected transition for this target, FIG. 2A (——). Significantly, when both protein targets are added to the solution of probes, the solution turns dark purple, and the melting analysis exhibits two distinct transactions. The first derivative of this curve shows two peaks centered at 36 and 55° C., respectively, FIG. 2B. This demonstrates that two distinct assemblies form and their melting properties, which derive from the oligonucleotide barcodes, can be used to distinguish two protein targets.

Figure 4:
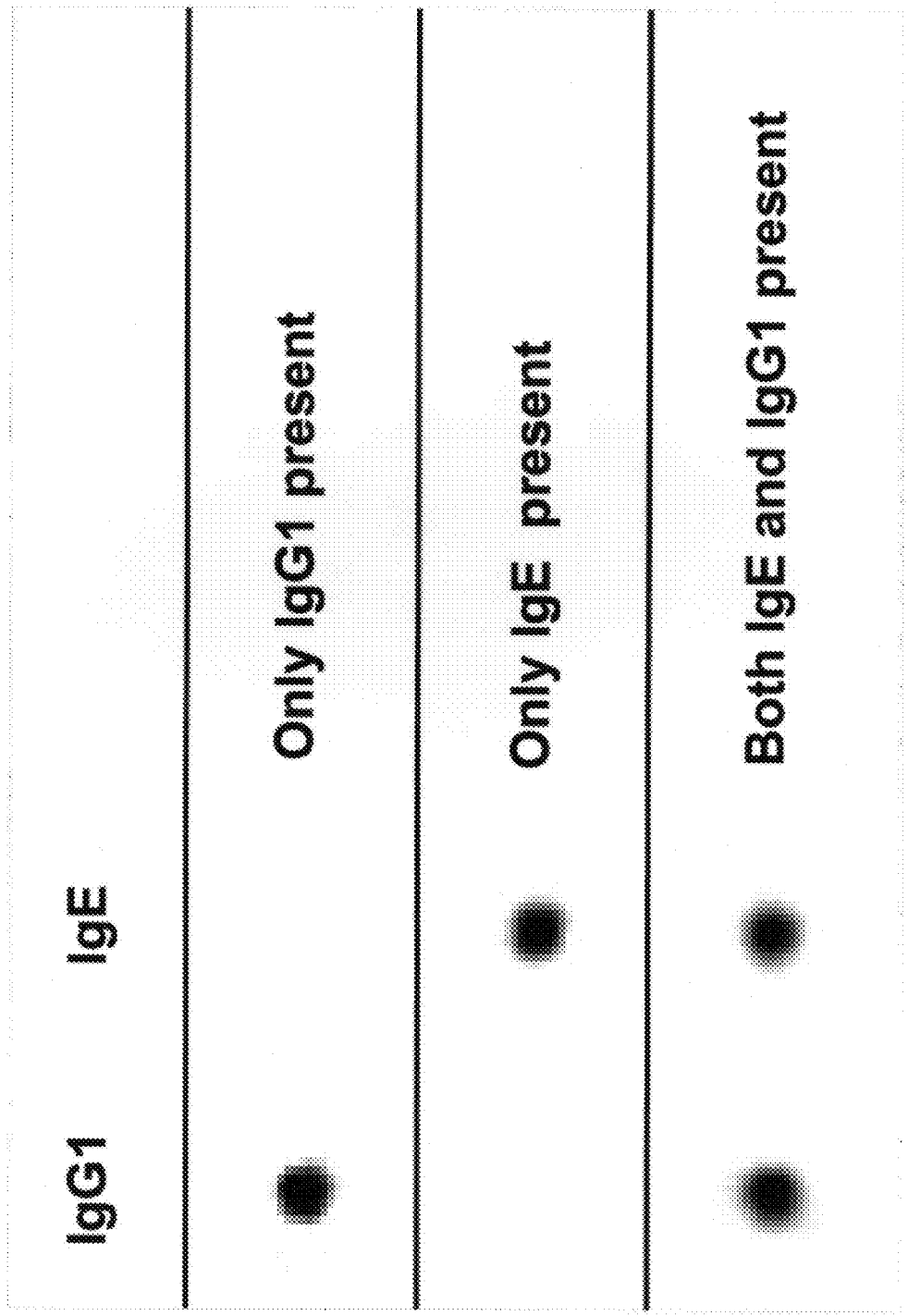
FIG. 4 illustrates scanometric DNA array detection of the DNA biobarcodes. Left column is for the detection of the biobarcode associated with IgG1 and the right column is for the biobarcode associated with IgE. The capture oligonucleotides are 5'-thiol-modified ATAACTAGAACTTGA for the IgG1 system and 5'-thiol-modifed TTATCTATTATT for the IgE system. Each spot is approximately 250 um in diameter and read via gray-scale with an Epson Expression 1640XL flatbed scanner (Epson America, Longbeach, Calif.). These assays have been studied and work comparably well over the 20 nM to 700 nM target concentration range.

In another aspect of the invention, a variation of the above aggregation method strategy can be used to increase the sensitivity of the aforementioned system and to increase the number of targets that can be interrogated in one solution. See, for instance, FIG. 3 in Example 4. With this strategy, the protein targets can be detected indirectly via the DNA biobarcodes or unique reporter oligonucleotides assigned to specific target analytes. Generally, the suitable length, GC content, and sequence, and selection of the reporter oligonucleotide for the target analyte is predetermined prior to the assay. For instance, a 12-mer oligonucleotide has $4^{12}$ different sequences, many of which can be used to prepare a barcode for a polyvalent protein of interest as shown in FIG. 1A. In this variation of the assay, the melting properties of the aggregates that form are not measured in solution but rather the reporter oligonucleotides or DNA biobarcodes within the aggregates are separated via centrifugation (e.g., 3000 rpm for 2 minutes) from the unreacted probes and target molecules. The aggregates are then denatured by any suitable means, e.g., by adding water to the solution, to free the reporter oligonucleotides or biobarcodes. If the reporter oligonucleotide is present in small amounts, it may be amplified by methods known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Preferred is polymerase chain reaction (PCR) amplification. The particles and proteins can be separated from the reporter oligonucleotides by any suitable means, e.g., a centrifugal filter device (Millipore Microcon YM-100, 3500 rpm for 25 min. Once the reporter oligonucleotides are isolated, they can be captured on an oligonucleotide array and can be identified using one of the many suitable DNA detection assays (FIG. 3). For the examples described herein involving IgG1 and IgE, the reporter oligonucleotides are captured on a microscope slide that has been functionalized with oligonucleotides (250 μm diameter spots) that are complementary to one half of the barcode of interest (A3 and B3 in FIG. 1). If the barcode is captured by the oligonucleotide array, a DNA-modified particle that is complementary to the remaining portion of the barcode can be hybridized to the array (see experimental section). When developed via the standard scanometric approach [11] (which involves treatment with photographic developing solution), a flat bed scanner can be used to quantify the results, FIG. 4.[11] If IgG1 is present, only the spot designed for IgG1 shows measurable signal. Similarly if IgE is the only protein present, the spot designed for it only exhibits signal. Finally, if both proteins are present, both spots exhibit intense signals.

The present invention is important because it provides two strategies for using nanoparticle probes (preferably gold nanoparticle probes), heavily functionalized with oligonucleotides, to detect single or multiple polyvalent proteins in one solution. Indeed, the detection of multiple proteins in one sample is not trivial and often requires time consuming, expensive assay protocols. In this regard, others have recently used fluorophore-labeled peptidonucleic acids and DNA microarrays to recognize multiple protein targets in one solution.[15-17] However, this method relies on the binding of the proteins labeled with oligonucleotides to a microarray surface. The final step of the method described herein is based solely on the surface chemistry of ordinary DNA. Therefore, it can incorporate many of the high sensitivity aspects of state-of-the-art nanoparticle DNA detection methods,[9,11] but allows one to detect proteins rather than DNA without having the proteins present during the detection event. For surface assays, proteins are typically more difficult to work with than short oligonucleotides because they tend to exhibit greater nonspecific binding to solid supports, which often leads to higher background signals. Finally, for the homogeneous assay, the unusually sharp melting profiles associated with these nanoparticle structures will allow one to design more biobarcodes than what would be possible with probes that exhibit normal and broad DNA melting behavior.

The present invention contemplates the use of any suitable particle having oligonucleotides attached thereto that are suitable for use in detection assays. In practicing this invention, however, nanoparticles are preferred. The size, shape and chemical composition of the particles will contribute to the properties of the resulting probe including the DNA barcode. These properties include optical properties, optoelectronic properties, electrochemical properties, electronic properties, stability in various solutions, pore and channel size variation, ability to separate bioactive molecules while acting as a filter, etc. The use of mixtures of particles having different sizes, shapes and/or chemical compositions, as well as the use of nanoparticles having uniform sizes, shapes and chemical composition, are contemplated. Examples of suitable particles include, without limitation, nano- and microsized core particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, which are incorporated by reference in their entirety.

Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm. The nanoparticles may also be rods, prisms, or tetrahedra.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Taransactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988).

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshavsky et al., *J. Am. Chem. Soc.*, 112, 9438 (1990); Ushida et al., *J. Phys. Chem.*, 95, 5382 (1992).

Suitable nanoparticles are also commercially available from, e.g., Ted Pella, Inc. (gold), Amersham Corporation (gold) and Nanoprobes, Inc. (gold).

Presently preferred for use in detecting nucleic acids are gold nanoparticles. Gold colloidal particles have high extinction coefficients for the bands that give rise to their beautiful colors. These intense colors change with particle size, concentration, interparticle distance, and extent of aggregation and shape (geometry) of the aggregates, making these materials particularly attractive for colorimetric assays. For instance, hybridization of oligonucleotides attached to gold nanoparticles with oligonucleotides and nucleic acids results in an immediate color change visible to the naked eye (see, e.g., the Examples).

The nanoparticles, the oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry*, Houston, Tex., pages 109-121 (1995). See also, Mucic et al. *Chem. Commun.* 555-557 (1996) (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lee et al., *J. Phys. Chem.*, 92, 2597 (1988) (rigid phosphates on metals).

U.S. patent application Ser. Nos. 09/760,500 and 09/820,279 and international application nos. PCT/US01/01190 and PCT/US01/10071 describe oligonucleotides functionalized with a cyclic disulfide which are useful in practicing this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

Preferably, the linker further comprises a hydrocarbon moiety attached to the cyclic disulfide. Suitable hydrocarbons are available commercially, and are attached to the cyclic disulfides Preferably the hydrocarbon moiety is a steroid residue. Oligonucleotide-nanoparticle conjugates prepared using linkers comprising a steroid residue attached to a cyclic disulfide have unexpectedly been found to be remarkably stable to thiols (e.g., dithiothreitol used in polymerase chain reaction (PCR) solutions) as compared to conjugates prepared using alkanethiols or acyclic disulfides as the linker. Indeed, the oligonucleotide-nanoparticle conjugates of the invention have been found to be 300 times more stable. This unexpected stability is likely due to the fact that each oligonucleotide is anchored to a nanoparticle through two sulfur atoms, rather than a single sulfur atom. In particular, it is thought that two adjacent sulfur atoms of a cyclic disulfide would have a chelation effect which would be advantageous in stabilizing the oligonucleotide-nanoparticle conjugates. The large hydrophobic steroid residues of the linkers also appear to contribute to the stability of the conjugates by screening the nanoparticles from the approach of water-soluble molecules to the surfaces of the nanoparticles.

In view of the foregoing, the two sulfur atoms of the cyclic disulfide should preferably be close enough together so that both of the sulfur atoms can attach simultaneously to the nanoparticle. Most preferably, the two sulfur atoms are adjacent each other. Also, the hydrocarbon moiety should be large so as to present a large hydrophobic surface screening the surfaces of the nanoparticles.

The oligonucleotide-cyclic nanoparticle conjugates that employ cyclic disulfide linkers may be used as probes in diagnostic assays for detecting target analytes in a sample as described in U.S. patent application Ser. Nos. 09/760,500 and 09/820,279 and international application nos. PCT/US01/01190 and PCT/US01/10071. These conjugates have been found to improve the sensitivity of diagnostic assays in which they are used. In particular, assays employing oligonucleotide-nanoparticle conjugates prepared using linkers comprising a steroid residue attached to a cyclic disulfide have been found to be about 10 times more sensitive than assays employing conjugates prepared using alkanethiols or acyclic disulfides as the linker.

Each nanoparticle will have a plurality of oligonucleotides attached to it. As a result, each nanoparticle-oligonucleotide conjugate can bind to a plurality of oligonucleotides or nucleic acids having the complementary sequence.

Oligonucleotides of defined sequences are used for a variety of purposes in the practice of the invention. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically. For oligonucleotides having bound thereto a specific binding complement to a target analyte, any suitable method for attaching the specific binding complement such as proteins to the oligonucleotide may be used.

Any suitable method for attaching oligonucleotides onto the nanosphere surface may be used. A particularly preferred method for attaching oligonucleotides onto a surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with unexpected enhanced stability and selectivity. The method comprises providing oligonucleotides preferably having covalently bound thereto a moiety comprising a functional group which can bind to the nanoparticles. The moieties and functional groups are those that allow for binding (i.e., by chemisorption or covalent bonding) of the oligonucleotides to nanoparticles. For instance, oligonucleotides having an alkanethiol, an alkanedisulfide or a cyclic disulfide covalently bound to their 5' or 3' ends can be used to bind the oligonucleotides to a variety of nanoparticles, including gold nanoparticles.

The oligonucleotides are contacted with the nanoparticles in water for a time sufficient to allow at least some of the oligonucleotides to bind to the nanoparticles by means of the functional groups. Such times can be determined empirically. For instance, it has been found that a time of about 12-24 hours gives good results. Other suitable conditions for binding of the oligonucleotides can also be determined empirically. For instance, a concentration of about 10-20 nM nanoparticles and incubation at room temperature gives good results.

Next, at least one salt is added to the water to form a salt solution. The salt can be any suitable water-soluble salt. For instance, the salt may be sodium chloride, magnesium chloride, potassium chloride, ammonium chloride, sodium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time has been found to give the highest surface density of oligonucleotides on the nanoparticles. Suitable ionic strengths can be determined empirically for each salt or combination of salts. A final concentration of sodium chloride of from about 0.1 M to about 1.0 M in phosphate buffer, preferably with the concentration of sodium chloride being increased gradually over time, has been found to give good results.

After adding the salt, the oligonucleotides and nanoparticles are incubated in the salt solution for an additional period of time sufficient to allow sufficient additional oligonucleotides to bind to the nanoparticles to produce the stable nanoparticle-oligonucleotide conjugates. As will be described in detail below, an increased surface density of the oligonucleotides on the nanoparticles has been found to stabilize the conjugates. The time of this incubation can be determined empirically. A total incubation time of about 24-48, preferably 40 hours, has been found to give good results (this is the total time of incubation; as noted above, the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results.

The conjugates produced by use of the "aging" step have been found to be considerably more stable than those produced without the "aging" step. As noted above, this increased stability is due to the increased density of the oligonucleotides on the surfaces of the nanoparticles which is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. Preferably, the surface density is at least 15 picomoles/cm$^2$. Since the ability of the oligonucleotides of the conjugates to hybridize with nucleic acid and oligonucleotide targets can be diminished if the surface density is too great, the surface density is preferably no greater than about 35-40 picomoles/cm$^2$.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

It has been found that the hybridization efficiency of nanoparticle-oligonucleotide conjugates can be increased dramatically by the use of recognition oligonucleotides which comprise a recognition portion and a spacer portion. "Recognition oligonucleotides" are oligonucleotides which comprise a sequence complementary to at least a portion of the sequence of a nucleic acid or oligonucleotide target. In this embodiment, the recognition oligonucleotides comprise a recognition portion and a spacer portion, and it is the recognition portion which hybridizes to the nucleic acid or oligonucleotide target. The spacer portion of the recognition oligonucleotide is designed so that it can bind to the nanoparticles. For instance, the spacer portion could have a moiety covalently bound to it, the moiety comprising a functional group which can bind to the nanoparticles. These are the same moieties and functional groups as described above. As a result of the binding of the spacer portion of the recognition oligonucleotide to the nanoparticles, the recognition portion is spaced away from the surface of the nanoparticles and is more accessible for hybridization with its target. The length and sequence of the spacer portion providing good spacing of the recognition portion away from the nanoparticles can be determined empirically. It has been found that a spacer portion comprising at least about 10 nucleotides, preferably 10-30 nucleotides, gives good results. The spacer portion may have any sequence which does not interfere with the ability of the recognition oligonucleotides to become bound to the nanoparticles or to a nucleic acid or oligonucleotide target. For instance, the spacer portions should not sequences complementary to each other, to that of the recognition olignucleotides, or to that of the nucleic acid or oligonucleotide target of the recognition oligonucleotides. Preferably, the bases of the nucleotides of the spacer portion are all adenines, all thymines, all cytidines, or all guanines, unless this would cause one of the problems just mentioned. More preferably, the bases are all adenines or all thymines. Most preferably the bases are all thymines.

It has further been found that the use of diluent oligonucleotides in addition to recognition oligonucleotides provides a means of tailoring the conjugates to give a desired level of hybridization. The diluent and recognition oligonucleotides have been found to attach to the nanoparticles in about the same proportion as their ratio in the solution contacted with the nanoparticles to prepare the conjugates. Thus, the ratio of the diluent to recognition oligonucleotides bound to the nanoparticles can be controlled so that the conjugates will participate in a desired number of hybridization events. The diluent oligonucleotides may have any sequence which does not interfere with the ability of the recognition oligonucleotides to be bound to the nanoparticles or to bind to a nucleic acid or oligonucleotide target. For instance, the diluent oligonulceotides should not have a sequence complementary to that of the recognition oligonucleotides or to that of the nucleic acid or oligonucleotide target of the recognition oligonucleotides. The diluent oligonucleotides are also preferably of a length shorter than that of the recognition oligonucleotides so that the recognition oligonucleotides can bind to their nucleic acid or oligonucleotide targets. If the recognition oligonucleotides comprise spacer portions, the diluent oligonulceotides are, most preferably, about the same length as the spacer portions. In this manner, the diluent oligonucleotides do not interefere with the ability of the recognition portions of the recognition oligonucleotides to hybridize with nucleic acid or oligonucleotide targets. Even more preferably, the diluent oligonucleotides have the same sequence as the sequence of the spacer portions of the recognition oligonucleotides.

For detection of the presence of a target analyte in a sample, particle complex probes, preferably nanoparticle complex probes, are used. These particle complexes may be generated prior to conducting the actual assay or in situ while conducting the assay. These complexes comprise a particle, preferably a nanoparticle, having oligonucleotides bound thereto, a reporter oligonucleotide, and an oligonucleotide having bound thereto a specific binding complement of a target analyte. The DNA barcode or reporter oligonucleotides has a sequence having at least two portions and joins via hybridization the nanoparticle having oligonucleotides bound thereto and the oligonucleotide having bound thereto the specific binding complement. The oligonucleotides bound to the nanoparticles have a sequence that is complementary to one portion of the reporter oligonucleotide and the oligonucleotide having bound thereto the specific binding complement having a sequence that is complementary to a second portion of the reporter oligonucleotide. The reporter oligonucleotides have at least two portions and joins via hybridization the nanoparticle having oligonucleotides bound thereto and the oligonucleotide having bound thereto the specific binding complement. When employed in a sample containing the target analyte, the nanoparticle complex binds to the target analyte and aggregation occurs. The aggregates may be isolated and subject to further melting analysis to identify the particular target analyte where multiple targets are present as discussed above. Alternatively, the aggregates can be dehybridized to release the reporter oligonucleotides. These reporter oligonucleotides can then be detected by any suitable DNA detection system using any suitable detection probes.

In another aspect of the invention, the reporter oligonucleotides released by dehybridization of the aggregates can be detected using a substrate having oligonucleotides bound thereto. The oligonucleotides have a sequence complementary to at least one portion of the reporter oligonucleotides. Some embodiments of the method of detecting the reporter oligonucleotides utilize a substrate having complementary oligonucleotides bound thereto to capture the reporter oligonucleotides. These captured reporter oligonucleotides are then detected by any suitable means. By employing a substrate, the detectable change (the signal) can be amplified and the sensitivity of the assay increased.

Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates).

Any suitable method for attaching oligonucleotides to a substrate may be used. For instance, oligonucleotides can be attached to the substrates as described in, e.g., Chrisey et al., *Nucleic Acids Res.*, 24, 3031-3039 (1996); Chrisey et al., *Nucleic Acids Res.*, 24, 3040-3047 (1996); Mucic et al., *Chem. Commun.*, 555 (1996); Zimmermann and Cox, *Nucleic Acids Res.*, 22, 492 (1994); Bottomley et al., *J. Vac. Sci. Technol. A*, 10, 591 (1992); and Hegner et al., *FEBS Lett.*, 336, 452 (1993).

The oligonucleotides attached to the substrate have a sequence complementary to a first portion of the sequence of reporter oligonucleotides to be detected. The reporter oligonucleotide is contacted with the substrate under conditions effective to allow hybridization of the oligonucleotides on the substrate with the reporter oligonucleotide. In this manner the reporter oligonucleotide becomes bound to the substrate. Any unbound reporter oligonucleotide is preferably washed from the substrate before adding a detection probe such as nanoparticle-oligonucleotide conjugates.

In one aspect of the invention, the reporter oligonucleotide bound to the oligonucleotides on the substrate is contacted with a first type of nanoparticles having oligonucleotides attached thereto. The oligonucleotides have a sequence complementary to a second portion of the sequence of the reporter oligonucleotide, and the contacting takes place under conditions effective to allow hybridization of the oligonucleotides on the nanoparticles with the reporter oligonucleotide. In this manner the first type of nanoparticles become bound to the substrate. After the nanoparticle-oligonucleotide conjugates are bound to the substrate, the substrate is washed to remove any unbound nanoparticle-oligonucleotide conjugates.

The oligonucleotides on the first type of nanoparticles may all have the same sequence or may have different sequences that hybridize with different portions of the reporter oligonucleotide to be detected. When oligonucleotides having different sequences are used, each nanoparticle may have all of the different oligonucleotides attached to it or, preferably, the different oligonucleotides are attached to different nanoparticles. Alternatively, the oligonucleotides on each of the first type of nanoparticles may have a plurality of different sequences, at least one of which must hybridize with a portion of the reporter oligonucleotide to be detected.

Optionally, the first type of nanoparticle-oligonucleotide conjugates bound to the substrate is contacted with a second type of nanoparticles having oligonucleotides attached thereto. These oligonucleotides have a sequence complementary to at least a portion of the sequence(s) of the oligonucleotides attached to the first type of nanoparticles, and the contacting takes place under conditions effective to allow hybridization of the oligonucleotides on the first type of nanoparticles with those on the second type of nanoparticles. After the nanoparticles are bound, the substrate is preferably washed to remove any unbound nanoparticle-oligonucleotide conjugates.

The combination of hybridizations produces a detectable change. The detectable changes are the same as those described above, except that the multiple hybridizations result in an amplification of the detectable change. In particular, since each of the first type of nanoparticles has multiple oligonucleotides (having the same or different sequences) attached to it, each of the first type of nanoparticle-oligonucleotide conjugates can hybridize to a plurality of the second type of nanoparticle-oligonucleotide conjugates. Also, the first type of nanoparticle-oligonucleotide conjugates may be hybridized to more than one portion of the reporter oligonucleotide to be detected. The amplification provided by the multiple hybridizations may make the change detectable for the first time or may increase the magnitude of the detectable change. This amplification increases the sensitivity of the assay, allowing for detection of small amounts of reporter oligonucleotide.

If desired, additional layers of nanoparticles can be built up by successive additions of the first and second types of nanoparticle-oligonucleotide conjugates. In this way, the number of nanoparticles immobilized per molecule of target nucleic acid can be further increased with a corresponding increase in intensity of the signal.

Also, instead of using first and second types of nanoparticle-oligonucleotide conjugates designed to hybridize to each other directly, nanoparticles bearing oligonucleotides that would serve to bind the nanoparticles together as a consequence of hybridization with binding oligonucleotides could be used.

When a substrate is employed, a plurality of the initial types of nanoparticle-oligonucleotide conjugates or oligonucleotides can be attached to the substrate in an array for detecting multiple portions of a target reporter oligonucleotide, for detecting multiple different reporter oligonucleotides, or both. For instance, a substrate may be provided with rows of spots, each spot containing a different type of oligonucleotide designed to bind to a portion of a target reporter oligonucleotide. A sample containing one or more reporter oligonucleotides is applied to each spot, and the rest of the assay is performed in one of the ways described above using appropriate oligonucleotide-nanoparticle conjugates.

Finally, when a substrate is employed, a detectable change can be produced or further enhanced by silver staining.

Silver staining can be employed with any type of nanoparticles that catalyze the reduction of silver. Preferred are nanoparticles made of noble metals (e.g., gold and silver). See Bassell, et al., *J. Cell Biol.*, 126, 863-876 (1994); Braun-Howland et al., *Biotechniques*, 13, 928-931 (1992). If the nanoparticles being employed for the detection of a nucleic acid do not catalyze the reduction of silver, then silver ions can be complexed to the nucleic acid to catalyze the reduction. See Braun et al., *Nature*, 391, 775 (1998). Also, silver stains are known which can react with the phosphate groups on nucleic acids.

Silver staining can be used to produce or enhance a detectable change in any assay performed on a substrate, including those described above. In particular, silver staining has been found to provide a huge increase in sensitivity for assays employing a single type of nanoparticle so that the use of layers of nanoparticles can often be eliminated.

In assays for detecting reporter oligonucleotides performed on a substrate, the detectable change can be observed with an optical scanner. Suitable scanners include those used to scan documents into a computer which are capable of operating in the reflective mode (e.g., a flatbed scanner), other devices capable of performing this function or which utilize the same type of optics, any type of greyscale-sensitive measurement device, and standard scanners which have been modified to scan substrates according to the invention (e.g., a flatbed scanner modified to include a holder for the substrate) (to date, it has not been found possible to use scanners operating in the transmissive mode). The resolution of the scanner must be sufficient so that the reaction area on the substrate is larger than a single pixel of the scanner. The scanner can be used with any substrate, provided that the detectable change produced by the assay can be observed against the substrate (e.g., a grey spot, such as that produced by silver staining, can be observed against a white background, but cannot be observed against a grey background). The scanner can be a black-and-white scanner or, preferably, a color scanner. Most preferably, the scanner is a standard color scanner of the type used to scan documents into computers. Such scanners are inexpensive and readily available commercially. For instance, an Epson Expression 636 (600×600 dpi), a UMAX Astra 1200 (300×300 dpi), or a Microtec 1600 (1600×1600 dpi) can be used. The scanner is linked to a computer loaded with software for processing the images obtained by scanning the substrate. The software can be standard software which is readily available commercially, such as Adobe Photoshop 5.2 and Corel Photopaint 8.0. Using the software to calculate greyscale measurements provides a means of quantitating the results of the assays. The software can also provide a color number for colored spots and can generate images (e.g., printouts) of the scans which can be reviewed to provide a qualitative determination of the presence of a nucleic acid, the quantity of a nucleic acid, or both. The computer can be a standard personal computer which is readily available commercially. Thus, the use of a standard scanner linked to a standard computer loaded with standard software can provide a convenient, easy, inexpensive means of detecting and quantitating nucleic acids when the assays are performed on substrates. The scans can also be stored in the computer to maintain a record of the results for further reference or use. Of course, more sophisticated instruments and software can be used, if desired.

A universal nanoparticle-oligonucleotide conjugate which may be used in an assay for any target reporter oligonucleotide. This "universal probe" has oligonucleotides of a single sequence attached to it and is complementary with a portion of the reporter oligonucleotide. These oligonucleotides bound to the universal probe can hybridize with a portion of the reporter oligonucleotides bound to the support. The first portion is complementary to at least a portion of the sequence of the oligonucleotides on the nanoparticles. The second portion is complementary to a portion of the sequence of the nucleic acid to be detected. A plurality of binding oligonucleotides having the same first portion and different second portions can be used, in which case the "universal probe", after hybridization to the binding oligonucleotides, can bind to multiple portions of the nucleic acid to be detected or to different nucleic acid targets.

It is to be noted that the term "a" or "an" entity refers to one or more of that entity. For example, "a characteristic" refers to one or more characteristics or at least one characteristic. As such, the terms "a" (or "an"), "one or more" and "at least one" are used interchangeably herein. It is also to be noted that the terms "comprising", "including", and "having" have been used interchangeably.

EXAMPLES

Example 1

Preparation of Oligonucleotide-Modified Gold Nanoparticles

A. Preparation Of Gold Nanoparticles

Oligonucleotide-modified 13 nm Au particles were prepared by literature methods (~110 oligonucleotides/particle)[18-20]. Gold colloids (13 nm diameter) were prepared by reduction of $HAuCl_4$ with citrate as described in Frens, *Nature Phys. Sci.*, 241, 20 (1973) and Grabar, *Anal. Chem.*, 67, 735 (1995). Briefly, all glassware was cleaned in aqua regia (3 parts HCl, 1 part $HNO_3$), rinsed with Nanopure $H_2O$, then oven dried prior to use. $HAuCl_4$ and sodium citrate were purchased from Aldrich Chemical Company. An aqueous solution of $HAuCl_4$ (1 mM, 500 mL) was brought to a reflux while stirring, and then 50 mL of a 38.8 mM trisodium citrate solution was added quickly, which resulted in a change in solution color from pale yellow to deep red. After the color change, the solution was refluxed for an additional fifteen minutes, allowed to cool to room temperature, and subsequently filtered through a Micron Separations Inc. 0.45 micron nylon filter. Au colloids were characterized by UV-vis spectroscopy using a Hewlett Packard 8452A diode array spectrophotometer and by Transmission Electron Microscopy (TEM) using a Hitachi 8100 transmission electron microscope. A typical solution of 13 nm diameter gold particles exhibited a characteristic surface plasmon band centered at 518-520 nm. Gold particles with diameters of 13 nm will produce a visible color change when aggregated with target and probe oligonucleotide sequences in the 10-72 nucleotide range.

B. Synthesis Of Oligonucleotides

Oligonucleotides were synthesized on a 1 micromole scale using a Milligene Expedite DNA synthesizer in single column mode using phosphoramidite chemistry. Eckstein, F. (ed.) *Oligonucleotides and Analogues: A Practical Approach* (IRL Press, Oxford, 1991). All solutions were purchased from Milligene (DNA synthesis grade). Average coupling efficiency varied from 98 to 99.8%, and the final dimethoxytrityl (DMT) protecting group was not cleaved from the oligonucleotides to aid in purification.

For 3'-thiol-oligonucleotides, Thiol-Modifier C3 S-S CPG support was purchased from Glen Research and used in the automated synthesizer. The final dimethoxytrityl (DMT) protecting group was not removed to aid in purification. After synthesis, the supported oligonucleotide was placed in 1 mL of concentrated ammonium hydroxide for 16 hours at 55° C. to cleave the oligonucleotide from the solid support and remove the protecting groups from the bases.

After evaporation of the ammonia, the oligonucleotides were purified by preparative reverse-phase HPLC using an HP ODS Hypersil column (5 μm, 250×4 mm) with 0.03 M triethyl ammonium acetate (TEAA), pH 7 and a 1%/minute gradient of 95% CH$_3$CN/5% 0.03 M TEAA at a flow rate of 1 mL/minute, while monitoring the UV signal of DNA at 254 nm. The retention time of the DMT protected modified 12-base oligomer was 30 minutes. The DMT was subsequently cleaved by soaking the purified oligonucleotide in an 80% acetic acid solution for 30 minutes, followed by evaporation; the oligonucleotide was redispersed in 500 μL of water, and the solution was extracted with ethyl acetate (3×300 μL). After evaporation of the solvent, the oligonucleotide (10 OD's) was redispersed in 100 υL of a 0.04 M DTT, 0.17 M phosphate buffer (pH 8) solution overnight at 50° C. to cleave the 3' disulfide. Aliquots of this solution (<10 OD's) were purified through a desalting NAP-5 column. The amount of oligonucleotide was determined by absorbance at 260 nm. Purity was assessed by ion-exchange HPLC using a Dionex Nucleopac PA-100 column (250×4 mm) with 10 mM NaOH (pH 12) and a 2%/minute gradient of 10 mM NaOH, 1 M NaCl at a flow rate of 1 mL/minute while monitoring the UV signal of DNA at 254 nm. Three peaks with retention times ($T_r$) of 18.5, 18.9 and 22 minutes were observed. The main single peak at $T_r$=22.0 minutes, which has been attributed to the disulfide, was 79% by area. The two peaks with shorter retention times of 18.5 and 18.9 minutes were ~9% and 12% by area respectively, and have been attributed to oxidized impurity and residual thiol oligonucleotide.

5'-Alkylthiol modified oligonucleotides were prepared using the following protocol: 1) a CPG-bound, detritylated oligonucleotide was synthesized on an automated DNA synthesizer (Expedite) using standard procedures; 2) the CPG-cartridge was removed and disposable syringes were attached to the ends; 3) 200 μL of a solution containing 20 μmole of 5-Thiol-Modifier C6-phosphoramidite (Glen Research) in dry acetonitrile was mixed with 200 μL of standard "tetrazole activator solution" and, via one of the syringes, introduced into the cartridge containing the oligonucleotide-CPG; 4) the solution was slowly pumped back and forth through the cartridge for 10 minutes and then ejected followed by washing with dry acetonitrile (2×1 mL); 5) the intermediate phosphite was oxidized with 700 μL of 0.02 M iodine in THF/pyridine/water (30 seconds) followed by washing with acetonitrile/pyridine (1:1; 2×1 mL) and dry acetonitirile. The trityloligonucleotide derivative was then isolated and purified as described by the 3'-alkylthiol oligonucleotides; then the trityl protecting group was cleaved by adding 15 υL (for 10 OD's) of a 50 mM AgNO$_3$ solution to the dry oligonucleotide sample for 20 minutes, which resulted in a milky white suspension. The excess silver nitrate was removed by adding 20 ΦL of a 10 mg/mL solution of DTT (five minute reaction time), which immediately formed a yellow precipitate that was removed by centrifugation. Aliquots of the oligonucleotide solution (<10 OD's) were then transferred onto a desalting NAP-5 column for purification. The final amount and the purity of the resulting 5' alkylthiol oligonucleotides were assessed using the techniques described above for 3' alkylthiol oligonucleotides. Two major peaks were observed by ion-exchange HPLC with retention times of 19.8 minutes (thiol peak, 16% by area) and 23.5 minutes (disulfide peak, 82% by area).

C. Attachment of Oligonucleotides to Gold Nanoparticles

A 1 mL solution of the gold colloids (17 nM) in water was mixed with excess (3.68 υM) thiol-oligonucleotide (22 bases in length) in water, and the mixture was allowed to stand for 12-24 hours at room temperature. Then, the solution was brought to 0.1 M NaCl, 10 mM phosphate buffer (pH 7) and allowed to stand for 40 hours. This "aging" step was designed to increase the surface coverage by the thiol-oligonucleotides and to displace oligonucleotide bases from the gold surface. The solution was next centrifuged at 14,000 rpm in an Eppendorf Centrifuge 5414 for about 25 minutes to give a very pale pink supernatant containing most of the oligonucleotide (as indicated by the absorbance at 260 nm) along with 7-10% of the colloidal gold (as indicated by the absorbance at 520 nm), and a compact, dark, gelatinous residue at the bottom of the tube. The supernatant was removed, and the residue was resuspended in about 200 μL of buffer (10 mM phosphate, 0.1 M NaCl) and recentrifuged. After removal of the supernatant solution, the residue was taken up in 1.0 mL of buffer (10 mM phosphate, 0.3 M NaCl, 0.01% NaN$_3$). The resulting red master solution was stable (i.e., remained red and did not aggregate) on standing for months at room temperature, on spotting on silica thin-layer chromatography (TLC) plates (see Example 4), and on addition to 1 M NaCl, 10 mM MgCl$_2$, or solutions containing high concentrations of salmon sperm DNA.

Example 2

Preparation of Hapten-Modified Oligonucleotides

Hapten-modified oligonucleotides were prepared with a biotin-triethylene glycol phosphoramidite for A1 and 2,4-dinitrophenyl-triethylene glycol phosphoramidite for B1 (Glen research) using standard solid-phase DNA synthesis procedures.[21]

Biotin modified oligonucleotides were prepared using the following protocol: A CPG-bound, detritylated oligonucleotide was synthesized on an automated DNA synthesizer (Expedite) using standard procedures[21]. The CPG-cartridge was then removed and disposable syringes were attached to the ends. 200 μL of a solution containing 20 μmole of biotin-triethylene glycol phosphoramidite in dry acetonitrile was then mixed with 200 μL of standard "tetrazole activator solution" and, via one of the syringes, introduced into the cartridge containing the oligonucleotide-CPG. The solution then was slowly pumped back and forth through the cartridge for 10 minutes and then ejected followed by washing with dry acetonitrile (2×1 mL). Thereafter, the intermediate phosphite was oxidized with 700 μL of 0.02 M iodine in THF/pyridine/water (30 seconds) followed by washing with acetonitrile/pyridine (1:1; 2×1 mL) and dry acetonitirile with subsequent drying of the column with a stream of nitrogen. The trityl protecting group was not removed, which aids in purification. The supported oligonucleotide was placed in 1 mL of concentrated ammonium hydroxide for 16 hours at 55° C. to cleave the oligonucleotide from the solid support and remove the protecting groups from the bases. After evaporation of the ammonia, the oligonucleotides were purified by preparative reverse-phase HPLC using an HP ODS Hypersil column (5 µm, 250×4 mm) with 0.03 M triethyl ammonium acetate (TEAA), pH 7 and a 1%/minute gradient of 95% CH$_3$CN/5% 0.03 M TEAA at a flow rate of 1 mL/minute, while monitoring the UV signal of DNA at 254 nm. The retention time of the DMT protected oligonucleotides was 32 minutes. The DMT was subsequently cleaved by soaking the purified oligonucleotide in an 80% acetic acid solution for 30 minutes, followed by evaporation; the oligonucleotide was redispersed in 500 µL of water, and the solution was extracted with ethyl acetate (3×300 µL) and dried. The same protocol was used to synthesize DNP modified oligonucleotide using 2,4-dinitrophenyl-triethylene glycol phosphoramidite.

Example 3

Assay Using Nanoparticle Complex Probes

The Oligonucleotide-modified 13 nm gold particles were prepared as described in Example 1. Hapten-modified oligonucleotides were prepared as described in Example 2 with a biotin-triethylene glycol phosphoramidite for A1 and 2,4-dinitrophenyl-triethylene glycol phosphoramidite for B1 (Glen research) using standard solid-phase DNA synthesis procedures.[21] The PBS buffer solution used in this research consists of 0.3 M NaCl and 10 mM phosphate buffer (pH 7). IgE and IgG1 were purchased from Sigma Aldrich (Milwaukee, Wis.) and dissolved in 0.3 M PBS buffer with 0.05% Tween 20 (final concentration: 4.3×10$^{-8}$ b/µl) and background proteins (10 ug/ml of lysozyme, 1% bovine serum albumin, and 5.3 ug/ml of anti-digoxin; 10 uL of each) prior to use.

To prepare the probes, the oligonucleotide modified particles (13 nM, 300 µL) were hybridized with hapten-modified complementary oligonucleotides (10 µL of 10 µM) and biobarcode DNA (10 µL of 10 µM) at room temperature for 2-3 h, sequences given in FIG. 1. Unreacted hapten-modified oligonucleotide and biobarcodes were removed via centrifugation (12,000 rpm, 20 min) of the nanoparticle probes and subsequent decanting of the supernatant.

In a typical assay for IgE and/or IgG1, the target proteins (40 µl of 43 µg/ml for each) were added to the solution containing the probes (~13 nM), and the mixture was incubated at 37° C. for 50 minutes to facilitate protein-hapten complexation. To ensure complete reaction among all the components, especially the complementary DNA strands, the solution was incubated to expedite hybridization at -15° C. for 20 minutes (Boekel Tropicooler Hot/Cold Block Incubator) and stored at 4° C. for 24 hours. If the target protein is present, particle aggregation takes place effecting a shift in the gold nanoparticle plasmon band and a red-to-purple color change along with precipitation. The hybridized products were centrifuged (3000 rpm for 2 minutes), and the supernatant containing unreacted elements was decanted prior to analysis. To determine which proteins are present, a melting analysis which monitors the extinction at 260 nm as a function of temperature is carried out in the solution, FIG. 2. When IgG1 is treated with the probes via the aforementioned protocol, the solution turns pinkish-blue, indicating the formation of nanoparticle aggregates. In a control experiment where no target but background proteins are present, there is no discernible precipitation. A melting analysis of the solution shows a sharp transition with a melting temperature (Tm) of 55° C. This is the expected transition for the IgG1 target, FIG. 2A (---). If IgE is added to a fresh solution of probes, the same color change is observed but the melting analysis provides a curve with a Tm of 36° C., the expected transition for this target, FIG. 2A (——). Significantly, when both protein targets are added to the solution of probes, the solution turns dark purple, and the melting analysis exhibits two distinct transactions. The first derivative of this curve shows two peaks centered at 36 and 55° C., respectively, FIG. 2B. This demonstrates that two distinct assemblies form and their melting properties, which derive from the oligonucleotide barcodes, can be used to distinguish two protein targets.

Example 4

Assay Using Nanoparticle Complex Probes

A variation of this strategy can be used to increase the sensitivity of the aforementioned system and to increase the number of targets that can be interrogated in one solution (FIG. 3). With this strategy, the protein targets can be detected indirectly via the DNA biobarcodes. A 12-mer oligonucleotide has 4$^{12}$ different sequences, many of which can be used to prepare a barcode for a polyvalent protein of interest via FIG. 1A. In this variation of the assay, the melting properties of the aggregates that form are not measured in solution but rather the DNA biobarcodes within the aggregates are separated via centrifugation (3000 rpm fro 2 minutes) from the unreacted probes and target molecules. The aggregates are then denatured by adding water to the solution, freeing the complexed DNA. The particles and proteins can be separated from the DNA barcodes with a centrifugal filter device (Millipore Microcon YM-100, 3500 rpm for 25 min). Once the DNA barcodes are isolated, they can be captured on an oligonucleotide array and can be identified using one of the many DNA detection assays (FIG. 3). For the examples described herein involving IgG1 and IgE, the barcodes are captured on a microscope slide that has been functionalized with oligonucleotides (250 µm diameter spots) that are complementary to one half of the barcode of interest (A3 and B3 in FIG. 1). If the barcode is captured by the oligonucleotide array, a DNA-modified particle that is complementary to the remaining portion of the barcode can be hybridized to the array (see experimental section). When developed via the standard scanometric approach [11] (which involves treatment with photographic developing solution), a flat bed scanner can be used to quantify the results, FIG. 4.[11] If IgG1 is present, only the spot designed for IgG1 shows measurable signal. Similarly if IgE is the only protein present, the spot designed for it only exhibits signal. Finally, if both proteins are present, both spots exhibit intense signals.

For scanometric DNA biobarcode detection, the DNA/Au nanoparticle assembly was centrifuged (3000 rpm for 2 min) in a polystyrene 1.5 mL vial, and the supernatant was removed. PBS buffer solution (700 µl) was added to the aggregate and the procedure was repeated to ensure isolation of the aggregate from unreacted protein and assay components. Then, 500 µl of water was added to the vial containing the aggregate to denature it. Microarrays were prepared and DNA hybridization methods were used according to literature methods.[11,22] The isolated DNA biobarcodes were premixed with A2-modified nanoparticles or B2-modified nanoparticles (2 nM), exposed to the DNA microarray, and incubated in a hybridization chamber (GRACE BIO-LABS) at room temperature for three hours. The array was then washed with 0.3M NaNO$_3$ and 10 nM NaH$_2$PO$_4$/Na$_2$HPO$_4$ buffer (pH 7) and submerged in Silver Enhancer Solution (Sigma) for three minutes at room temperature. The slide was washed with water and then analyzed with a flat bed scanner.

REFERENCES (1) A. Pandey and M. Mann, *Nature* 2000, 405, 837-846.
(2) S. Fields and O. K. Song, *Nature* 1989, 340, 245-246.
(3) M. Ijksma, B. Kamp, J. C. Hoogvliet, W. P. van Bennekom, *Anal. Chem.* 2001, 73, 901-907.
(4) R. F. Service, *Science*, 2000, 287, 2136-2138.
(5) H. Zole, *Monoclonal Antibodies*, Springer-Verlag, New York, 2000, p. 1-5.
(6) J. E. Butler, *J. Immunoassay*, 2000, 21(2 & 3), 165-209.
(7) P. Herbrink, A. Noorduyn, W. C. Van Dijk, *Tech. Diagn. Pathol.* 1991, 2, 1-19.
(8) C. A. Mirkin, R. L. Letsinger, R. C. Mucic, J. J. Storhoff, *Nature* 1996, 382, 607-609
(9) J. J. Storhoff, C. A. Mirkin, *Chem. Rev.* 1999, 99, 1849-1862.
(10) S.-J. Park, A. A. Lazarides, C. A. Mirkin, P. W. Brazis, C. R. Kannewurf, R. L. Letsinger, *Angew. Chem. Int. Ed.* 2000, 39, 3845-3848.
(11) T. A. Taton, C. A. Mirkin, and R. L. Letsinger, *Science* 2000, 289, 1757-1760.
(12) S.-J. Park, A. A. Lazarides, C. A. Mirkin, and R. L. Letsinger, *Angew. Chem. Int. Ed.* 2001, 40, 2909-2912.
(13) Z. Eshhar, M. Ofarim, and T. Waks, *J. Immunol.* 1980, 124, 775-780.
(14) M. Wilcheck and E. A. Bayer, *Immunol. Today* 1984, 5, 39-43
(15) N. Winssinger, J. L. Harris, B. J. Backes, P. G. Schultz, *Agnew. Chem. Int. Ed.* 2001, 40, 3152-3155
(16) G. MacBeath, A. N. Koehler, S. L. Schreiber, *J. Am. Chem. Soc.* 1999, 121, 7967-7968.
(17) P. J. Hergenrother, K. M. Depew, S. L. Schreiber, *J. Am. Chem. Soc.* 2000, 122, 7849-7850.
(18) J. J. Storhoff, R. Elghanian, R. C. Mucic, C. A. Mirkin, R. L. Letsinger, *J. Am. Chem. Soc.* 1998, 120, 1959-1964.
(19) R. C. Mucic, J. J. Storhoff, C. A. Mirkin, R. L. Letsinger, *J. Am. Chem. Soc.* 1998, 120, 12674-12675.
(20) L. M. Demers, C. A. Mirkin, R. C. Mucic, R. A. Reynolds III, R. L. Letsinger, R. Elghanian, G. Viswanadham, Anal. Chem. 2000, 72, 5535-5541.
(21) T. Brown, D. J. S. Brown, in *Oligonucleotides and Analogues* (Ed.: F. Eckstein), Oxford University Press, New York, 1991.
(22) L. A. Chrisey, G. U. Lee, and C. E. O'Ferral, *Nucl. Acids. Res.* 1996, 24, 3031-3039.
(23) Nicewarner-Pena, S. R. Freeman, R. G.; Reiss, B. D.; He, L.; Pena, D. J.; Walton, I. D.; Cromer, R.; Keating, C. D.; Natan M. J. Science 2001, 294, 137.
(24) Ferguson, J. A.; Steemers, F. J.; Walt, D. R. Anal. Chem. 2000, 72, 5618.
(25) Han, M.; Gao, X.; Nie, S. Nature biotech. 2001, 19, 631.

What is claimed:

1. A method for detecting for the presence of one or more target non-nucleic acid analytes in a sample comprising:
providing one or more types of particle complex probes, each probe comprising a particle having oligonucleotides bound thereto, a DNA barcode, and a oligonucleotide having bound thereto a specific binding complement to a target analyte, wherein (i) the DNA barcode has a sequence having at least two portions, (ii) at least some of the oligonucleotides attached to the particle have a sequence that is complementary to a first portion of the DNA barcode, (iii) the oligonucleotides having bound thereto a specific binding complement have a sequence that is complementary to a second portion of the DNA barcode, and (iv) the DNA barcode in each type of particle complex probe has a sequence that is different and that serves as an identifier for a particular target analyte; wherein the DNA barcode is hybridized at least to some of the oligonucleotides attached to the particle and to the oligonucleotides having bound thereto the specific binding complement;

contacting the sample with a particle complex probe under conditions effective to allow specific binding interactions between the analyte and the particle complex probe and to form one or more aggregated complexes in the presence of analytes;

observing whether aggregate formation occurred;

isolating the aggregated complexes; and analyzing the aggregated complexes by measuring melting temperature (Tm) of the aggregated complexes to determine presence of one or more target non-nucleic acid analytes.

2. The method of claim 1, wherein the target analyte is one or more antibodies and the specific binding complement is a hapten.

3. The method of claim 1, wherein the target analyte and the specific binding component are members of a specific binding pair.

4. The method of claim 3, wherein the specific binding pair comprises a ligand and receptor.

5. The method of claim 3, wherein the specific binding pair comprises an antibody and an antigen.

6. The method of claim 1, wherein the target analyte is a monovalent or a polyvalent ligand.

7. The method of claims 1 or 2, wherein the particles are nanoparticles.

8. The method of claims 1 or 2, wherein the particles are metal, semiconductor, insulator, or magnetic nanoparticles.

9. The method of claims 1 or 2, wherein the particles are gold nanoparticles.

* * * * *

```
                        SEQUENCE LISTING

<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 1
ataactagaa cttga                                                      15

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 2
ttatctatta tt                                                         12

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 3
aaaaaaaaaa ataactagaa cttga                                           25
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:random
       synthetic sequence

<400> SEQUENCE: 4
tctgaattga ttacgaaaaa aaaaa                                        25

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:random
       synthetic sequence

<400> SEQUENCE: 5
cgtaatcaat tcagatcaag ttctagttat                                   30

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:random
       synthetic sequence

<400> SEQUENCE: 6
aaaaaaaaaa ttatctatta tt                                           22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:random
       synthetic sequence

<400> SEQUENCE: 7
ttatatgatt ataaaaaaaa aa                                           22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:random
       synthetic sequence

<400> SEQUENCE: 8
ataatcatat aaaataatag ataa                                         24